(12) United States Patent
Suzuki et al.

(10) Patent No.: US 6,395,503 B1
(45) Date of Patent: May 28, 2002

(54) CHEMILUMINESCENT REAGENTS AND CHEMILUMINESCENCE ANALYSIS METHODS WITH THE USE OF THE SAME

(75) Inventors: Hideaki Suzuki; Kiyoshi Takahashi; Gen-ichiro Araya; Hisashi Katsuragi; Mio Hosogoe, all of Tokyo (JP)

(73) Assignee: Dainichiseika Color & Chemicals Mfg. Co., Ltd., Tokyo (JP)

( * ) Notice: Subject to any disclaimer, the term of this patent is extended or adjusted under 35 U.S.C. 154(b) by 0 days.

(21) Appl. No.: 09/529,546

(22) PCT Filed: Aug. 13, 1999

(86) PCT No.: PCT/JP99/04401
§ 371 (c)(1),
(2), (4) Date: Apr. 14, 2000

(87) PCT Pub. No.: WO00/09626
PCT Pub. Date: Feb. 24, 2000

(30) Foreign Application Priority Data

Aug. 14, 1998 (JP) .............................. 10-244404
Aug. 14, 1998 (JP) .......................... 10-244424
Aug. 14, 1998 (JP) .......................... 10-244428
Dec. 18, 1998 (JP) .......................... 10-361569
Dec. 18, 1998 (JP) .......................... 10-361570
Dec. 18, 1998 (JP) .......................... 10-361571

(51) Int. Cl.$^7$ ..................... C12A 1/28; G01N 33/533; G01N 33/76
(52) U.S. Cl. ..................... 435/28; 435/7.4; 435/7.9; 435/7.92; 436/546; 436/800; 436/817; 436/818
(58) Field of Search ................. 436/546, 800, 436/817, 818; 435/7.9, 7.92, 7.4, 28

(56) References Cited

U.S. PATENT DOCUMENTS 4,277,437 A * 7/1981 Maggio 5,866,335 A * 2/1999 Katsilometes et al.

FOREIGN PATENT DOCUMENTS

JP A10300674 11/1998

OTHER PUBLICATIONS

Ahlberg et al., Journal of American Chemical Society, vol. 10 pp. 844–849 (1981).
Papadopoulos et al., Journal of Photochemistry and Photobiology, vol. 124, pp. 85–90 (1999).

* cited by examiner

Primary Examiner—Mary E. Ceperley
(74) Attorney, Agent, or Firm—Birch, Stewart, Kolasch & Birch, LLP

(57) ABSTRACT

The present invention provides a novel chemiluminescent reagent producing chemiluminescence in the presence of hydrogen peroxide, extent of which depends on peroxidase concentration, chemiluminescent analysis method using the same, in particular useful for detection and quantitative analysis of various types of materials by measuring peroxidase enzyme activity or enzyme immunoassay with peroxidase enzyme as the marker.

More particularly, the present invention provides a chemiluminescent reagent containing, as the major ingredients, a charge-transferring complex of N,N'-disubstituted-9,9'-bisacridinium salt and N,N-disubstituted carboxylic amide compound; chemiluminescent reagent containing further containing a specific aminoalcohol compound, in addition to the above; and method for measuring peroxidase activity at a high sensitivity in the presence of a peroxide, using the above chemiluminescent reagent.

Moreover, the novel chemiluminescent reagent of the present invention can enhance sensitivity of the enzyme immunoassay with peroxidase enzyme as the marker by its chemiluminescent reaction.

20 Claims, 4 Drawing Sheets

CHEMILUMINESCENT REAGENTS AND CHEMILUMINESCENCE ANALYSIS METHODS WITH THE USE OF THE SAME

This application is the national phase under 35 U.S.C. § 371 of PCT International Application No. PCT/JP99/04401 which has an International filing date of Aug. 13, 1999, which designated the United States of America.

FIELD OF THE INVENTION

This invention relates to a chemiluminescent reagent capable of giving controlled chemiluminescence, useful for, e.g., detection or quantitative analysis of a variety of materials by the chemiluminescent analysis. This invention also relates to a method for measuring peroxidase activity in the presence of a hydrogen acceptor by the chemiluminescent analysis using the above chemiluminescent reagent, and chemiluminescent enzyme immunoassay using peroxidase as the marker.

BACKGROUND TECHNIQUES

Lucigenin (N,N'-dimethyl-9,9'-bisacridinium dinitrate), which has been widely used for a long time for a variety of microanalysis methods as a chemiluminescent reagent, is known to generate light slightly in an aqueous alkaline solution and strongly in the presence of hydrogen peroxide. It can be used to quantitatively analyze hydrogen peroxide, because it emits light quantitatively in the presence of hydrogen peroxide and an alkali, but is difficult to apply to chemiluminescent enzyme immunoassay (hereinafter referred to as CLEIA, as necessary), which measures enzyme activity by extent of luminescence it produces by its reaction while controlling the luminescence. One of the methods proposed to solve these problems uses glucose oxidase as the marker enzyme to produce chemiluminescence, extent of which depends on concentration of the material to be analyzed, by acting hydrogen peroxide, as the product of glucose oxidation, on lucigenin in the presence of an alkali.

However, the CLEIA method with glucose oxidase as the marker involves problems of time-consuming reagent preparation and handling of the luminescent system. Luminol is used as the chemiluminescent reagent applicable to the CLEIA method with peroxidase, which can be handled relatively easily, as the marker. However, it cannot always show sufficient sensitivity, even in the presence of luminescent promoter, e.g., p-iodophenol.

Therefore, there are increasing demands for chemiluminescent reagents which can be prepared easily, simplify the luminescent analysis procedure, are applicable to the CLEIA method with peroxidase as the marker, and realize high-sensitivity analysis.

It is also necessary to further improve sensitivity of the CLEIA method with peroxidase as the marker, because it is required to quantitatively cover increasingly lower concentrations of the materials to be analyzed.

DISCLOSURE OF THE INVENTION

It is an object of the present invention to provide a novel chemiluminescent reagent for chemiluminescence appearing depending on molar concentration of peroxidase with the substrate of a peroxide, e.g., hydrogen peroxide, as the hydrogen acceptor.

It is another object of the present invention to provide a chemiluminescent reagent which produces a high extent of chemiluminescence and is highly stable.

It is still another object of the present invention to provide a novel analysis based on the chemiluminescence which uses the above chemiluminescent reagent to measure peroxidase activity at higher sensitivity.

It is still another object of the present invention to provide a novel chemiluminescent enzyme immunoassay by the new immunoassay system, developed on the basis of the chemiluminescence which uses the above chemiluminescent reagent and peroxidase enzyme as the marker to measure a material to be analyzed at higher sensitivity.

The inventors of the present invention have found, after having extensively studied to achieve the above objects, that a chemiluminescent reagent which contains a charge-transferring complex of N,N'-disubstituted-9,9'-bisacridinium salt and N,N-disubstituted carboxylic amide compound, a chemiluminescent reagent obtained by incorporating an aminoalcohol compound into the above chemiluminescent regent, a chemiluminescent reagent prepared by reacting an N,N'-disubstituted-9,9'-bisacridinium salt with N,N-disubstituted carboxylic amide compound while being irradiated with light, or a chemiluminescent reagent prepared by reacting an N,N'-disubstituted-9,9'-bisacridinium salt with N,N-disubstituted carboxylic amide compound while being irradiated with light, wherein an aminoalcohol compound is added to the reaction system during and/or after the charge-transfer reaction do not react with hydrogen peroxide at a specific pH level but produce chemiluminescence in the simultaneous presence of hydrogen peroxide and peroxidase to an extent determined by molar concentration of the peroxidase, reaching the present invention.

First, the present invention relates to a chemiluminescent reagent (hereinafter referred to as Chemiluminescent Reagent I, as necessary) characterized by the chemiluminescence produced in the presence of a peroxide, extent of which varies depending on concentration of peroxidase enzyme, which comprises, as the major ingredients, a charge-transferring complex of N,N'-disubstituted-9,9'-bisacridinium salt, shown by the general formula (1):

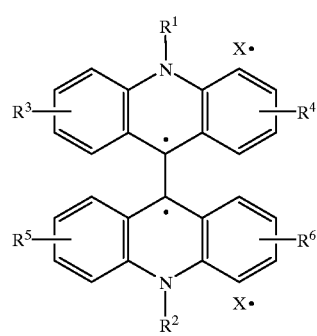

(1)

(wherein, $R^1$ and $R^2$ are each selected from the group consisting of an alkyl, aryl and halogenated aryl groups, and may be the same or different; $R^3$, $R^4$, $R^5$ and $R^6$ are each selected from the group consisting of hydrogen, an alkyl, aryl, alkoxy and aryloxy groups and haolgen, and may be the same or different; and X. is an acid radical as the residue left by the electron transferring from the counter anion of the bisacridinium salt as the precursor), and an N,N- disubstituted carboxylic amide compound shown by the general formula (2):

(2)

(wherein, $R^1$ is selected from the group consisting of hydrogen, an alkyl group having a carbon number of 1 to 10, an alkenyl group having a carbon number of 2 to 10 and an aryl group having a carbon number of 6 to 20, wherein the aryl group may be substituted with an alkyl, nitro, hydroxyl or amino groups, halogen or the like; $R_2$ is selected from the group consisting of methyl and ethyl groups; and $R_3$ is selected from the group consisting of an alkyl group having a carbon number of 1 to 10, an alkenyl group having a carbon number of 2 to 10 and an aryl group having a carbon number of 6 to 20, wherein the aryl group may be substituted with an alkyl, nitro, hydroxyl or amino groups, halogen or the like, and $R_1$ and $R_3$ may be bonded to each other to form a ring together with the carbon atom and nitrogen atom which are in the carbonyl and amide groups, respectively, to which each of $R_1$ and $R_3$ are bonded).

Second, the present invention relates to a chemiluminescent reagent (hereinafter referred to as Chemiluminescent Reagent II, as necessary) characterized by the chemiluminescence produced in the presence of a peroxide, extent of which varies depending on concentration of peroxidase enzyme, which comprises, as the major ingredients, a charge-transferring complex of N,N'-disubstituted-9,9'-bisacridinium salt shown by the general formula (1), N,N-disubstituted carboxylic amide compound shown by the general formula (2) and aminoalcohol compound shown by the general formula (3)

(3)

(wherein, R is a divalent aliphatic hydrocarbon group having a carbon number of 1 to 5; and (m) is an integer of 1 to 3).

Third, the present invention relates to a chemiluminescent reagent (hereinafter referred to as Chemiluminescent Reagent III, as necessary) prepared by reacting, in the presence of irradiated light, an N,N'-disubstituted-9,9'-bisacridinium salt shown by the general formula (1A):

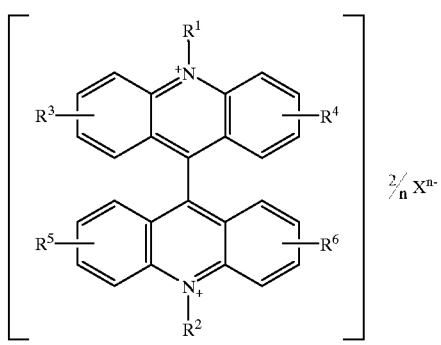
(1A)

(wherein, $R^1$ and $R^2$ are each selected from the group consisting of an alkyl, aryl and halogenated aryl groups, and may be the same or different; $R^3$, $R^4$, $R^5$ and $R^6$ are each selected from the group consisting of hydrogen, an alkyl, aryl, alkoxy and aryloxy groups and haolgen, and may be the same or different; and $X^{n-}$ is an n-valent anion; and (n) is 1 or 2) with an N,N-disubstituted carboxylic amide compound shown by the general formula (2):

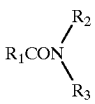
(2)

(wherein, $R^1$ is selected from the group consisting of hydrogen, an alkyl group having a carbon number of 1 to 10, an alkenyl group having a carbon number of 2 to 10 and an aryl group having a carbon number of 6 to 20, wherein the aryl group may be substituted with an alkyl, nitro, hydroxyl or amino groups, halogen or the like; $R_2$ is selected from the group consisting of methyl and ethyl groups; and $R_3$ is selected from the group consisting of an alkyl group having a carbon number of 1 to 10, an alkenyl group having a carbon number of 2 to 10 and an aryl group having a carbon number of 6 to 20, wherein the aryl group may be substituted with an alkyl, nitro, hydroxyl or amino group, halogen or the like, and $R^1$ and $R_3$ may be bonded to each other to form a ring together with the carbon atom and nitrogen atom which are in the carbonyl and amide groups, respectively, to which each of $R^1$ and $R_3$ are bonded).

Fourth, the present invention relates to a chemiluminescent reagent (hereinafter referred to as Chemiluminescent Reagent IV, as necessary) prepared by reacting an N,N'-disubstituted-9,9'-bisacridinium salt shown by the general formula (1A) with an N,N-disubstituted carboxylic amide compound shown by the general formula (2) while being irradiated with light, wherein an aminoalcohol compound shown by the general formula (3)

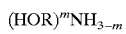
(3)

(wherein, R is a divalent aliphatic hydrocarbon group having a carbon number of 1 to 5; and (m) is an integer of 1 to 3).is added to the reaction system during and/or after the charge-transfer reaction.

Fifth, the present invention relates to a method for measuring peroxidase activity in the presence of a hydrogen acceptor by the chemiluminescent analysis using one of the above chemiluminescent reagents of the present invention.

Sixth, the present invention relates to a chemiluminescent enzyme immunoassay, which comprises mixing an antibody or antigen marked with peroxidase enzyme with an antibody, antigen or agglomerate thereof in a sample to be analyzed to form the immune complex from the marker/antigen-antibody complex by the antigen-antibody reaction, separating the immune complex, producing its chemiluminescence in the presence of a hydrogen acceptor by the aid of the above chemiluminescent reagent, and measuring the luminescence intensity to quantitatively analyze the anti-gen or antibody in the sample.

DESCRIPTION OF THE PREFERRED EMBODIMENTS

Figure 1:
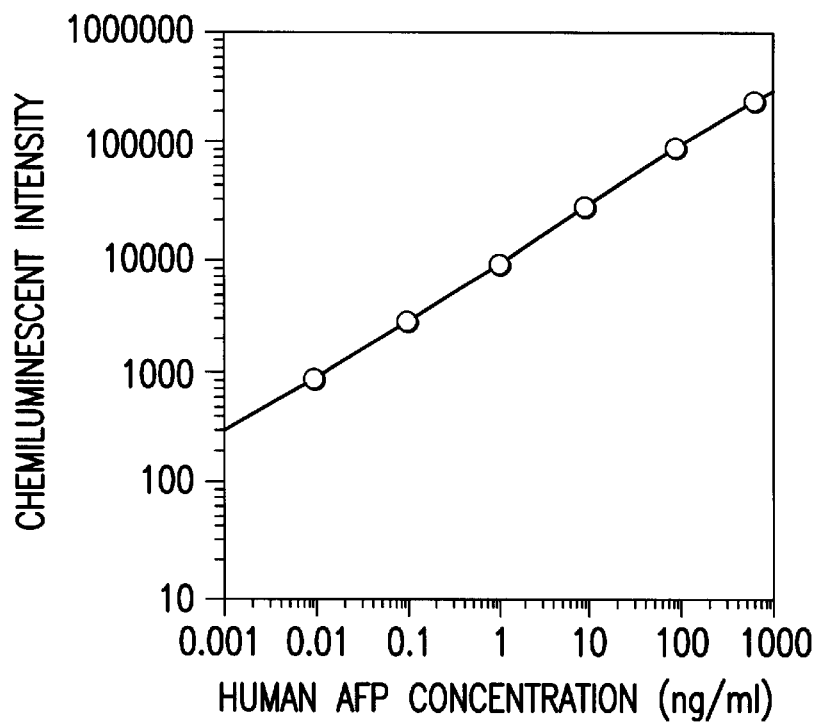
FIG. 1 is a calibration curve for measuring human α-fetoprotein (human αAFT) as the standard, plotting chemiluminescence intensity of the reaction system of EXAMPLE 1-2 against concentration of human αAFT.

The present invention is described more concretely.
Chemiluminescent Reagents

Chemiluminescent Reagent I of the present invention comprises, as the major ingredients, a charge-transferring complex of N,N'-disubstituted-9,9'-bisacridinium salt and N,N-disubstituted carboxylic amide compound, wherein "the major ingredients" means that the charge-transferring complex of N,N'-disubstituted-9,9'-bisacridinium salt and N,N-disubstituted carboxylic amide compound account for 50 wt. % or more on the total weight of the chemiluminescent reagent, preferably 70 wt. % or more. The reagent may contain other substances, e.g., by-product associated with the production process.

The charge-transferring complex of N,N'-disubstituted-9, 9'-bisacridinium salt, as one of the major ingredients, is shown by the general formula (1):

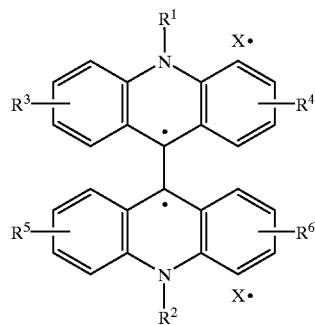

(1)

In the general formula (1), $R^1$ and $R^2$ are each selected from the group consisting of an alkyl, aryl and halogenated aryl groups, and may be the same or different. Each of the alkyl, aryl and halogenated aryl groups has a carbon number of 1 to 20, preferably 1 to 10 in the case of the alkyl group. The preferable alkyl groups include straight-chain and branched methyl, ethyl, propyl, butyl, pentyl, hexyl, heptyl, octyl, nonyl and decyl groups. The preferable aryl groups are those having a carbon number of 6 to 20, including phenyl, toryl and xylyl groups. They may be substituted by an alkyl group. Phenyl group is more preferable. The preferable halogenated aryl groups include halogenated phenyl, tolyl and xylyl groups, of which chlorophenyl group is more preferable.

In the general formula (1), $R^3$, $R^4$, $R^5$ and $R^6$ are each selected from the group consisting of hydrogen, an alkyl, aryl, alkoxy and aryloxy groups and haolgen, and may be the same or different. These hydrocarbon groups have a carbon number of 1 to 20, preferably 1 to 10. More concretely, these include straight-chain or branched alkyl and alkoxy groups having a carbon number of 1 to 20, and an aryl and aryloxy groups having a carbon number of 6 to 20, where the aryl and aryloxy group may be substituted with an alkyl group.

The preferred embodiments have an alkyl group having a carbon number of 1 to 10, or an aryl or halogenated aryl groups having a carbon number of 6 to 20 for each of $R^1$ and $R^2$, and hydrogen atom for each of $R^3$, $R^4$, $R^5$ and $R^6$.

In the general formula (1), X. is an acid radical as the residue left by the electron transferring from the counter anion of the bisacridinium salt as the precursor.

The charge-transferring complex of N,N'-disubstituted-9, 9'-bisacridinium salt is represented by a broad absorption band having a maximum at around 550 nm in the ultraviolet absorption spectroscopy, which can be measured by a spectrophotometer.

More concretely, the charge-transferring complex of N,N'-disubstituted-9,9'-bisacridinium salts include each charge-transferring complex of N,N'-dimethyl-9,9'-bisacridinium, N,N'-diethyl-9,9'-bisacridinium, N,N'-dipropyl-9,9'-bisacridinium, N,N'-diisopropyl-9,9'-bisacridinium, N,N'-dibutyl-9,9'-bisacridinium, N,N'-diisobutyl-9,9'-bisacridinium, N,N'-diphenyl-9,9'-bisacridinium, and N,N'-di-m-chlorophenyl-9,9'-bisacridinium salts.

The counter ions in the N,N'-disubstituted-9,9'-bisacridinium salt as the precursor for the charge-transferring complexes of N,N'-disubstituted-9,9'-bisacridinium salt include, but not limited to, chlorine, bromine, iodine, nitrate, carbonate, sulfate, phosphate and carbonate ions. Therefore, the preferable precursors for the charge-transferring complex of N,N'-disubstituted-9,9'-bisacridinium salt include N,N'-dimethyl-9,9'-bisacridinium dihydrochloride, N,N'-dimethyl-9,9'-bisacridinium dihydroiodide and N,N'-dimethyl-9,9'-bisacridinium dinitrate, of which N,N'-dimethyl-9,9'-bisacridinium dinitrate (Lucigenin) is preferable.

The N,N-disubstituted carboxylic amide compound, as the other major ingredient for Chemiluminescent Reagent I, is shown by the general formula (2):

(2)

In the general formula (2), $R_1$ is selected from the group consisting of hydrogen, an alkyl group having a carbon number of 1 to 10, an alkenyl group having a carbon number of 2 to 10 and an aryl group having a carbon number of 6 to 20, wherein the aryl group may be substituted with an alkyl, nitro, hydroxyl or amino groups, halogen or the like; $R_2$ is selected from the group consisting of methyl and ethyl groups; and $R_3$ is selected from the group consisting of an alkyl group having a carbon number of 1 to 10, an alkenyl group having a carbon number of 2 to 10 and aryl group having a carbon number of 6 to 20, wherein the aryl group may be substituted with an alkyl, nitro, hydroxyl or amino group, halogen or the like, and $R_1$ and $R_3$ may be bonded to each other to form a ring together with the carbon atom and nitrogen atom which are in the carbonyl and amide groups, respectively, to which each of $R_1$ and $R_3$ are bonded.

More concretely, the N,N-disubstituted carboxylic amide compounds include, but not limited to, N,N-dimethylformamide, N,N-dimethylacetoamide, N,N-dimethylacrylamide, N,N-dimethylpropionamide, N,N-dimethylbenzamide and N-methyl-2-pyrrolidone.

Chemiluminescent Reagent I of the present invention contains, as described above, a charge-transferring complex of N,N'-disubstituted-9,9'-bisacridinium salt and N,N-disubstituted carboxylic amide compound as the essential ingredients. An N,N'-disubstituted-9,9'-bisacridinium salt as the precursor for the charge-transferring complex as one of the essential ingredients for the reagent is found to convert itself from the highly ionic salt to the highly radical charge-transferring complex in the presence of an N,N-disubstituted carboxylic amide compound as the other essential ingredient, when irradiated with light. This phenomenon is explained by the accelerated charge transfer to the N,N'-disubstituted-9,9'-bisacridinium cation from the counter anion. It is also considered that the N,N-disubstituted carboxylic amide compound helps stabilize the radicals of the charge-transferring complex formed, working as the essential ingredient for forming and stabilizing the charge-transferring complex of N,N'-disubstituted-9,9'-bisacridinium salt, composed of the acid of weak nuclephilicity.

The molar ratio of the N,N-disubstituted carboxylic amide compound to charge-transferring complex of N,N'-disubstituted-9,9'-bisacridinium salt for Chemiluminescent Reagent I is 1 to 10,000, preferably 1 to 5,000.

Chemiluminescent Reagent II of the present invention contains, as the major ingredients, a charge-transferring complex of N,N'-disubstituted-9,9'-bisacridinium salt, N,N-disubstituted carboxylic amide compound and an aminoalcohol compound, wherein these major ingredients account for 50 wt. % or more on the total weight of chemiluminescent reagent, preferably 70 wt. % or more. The reagent may contain other substances, e.g., by-product associated with the production process, as is the case with Chemiluminescent Reagent I. The N,N'-disubstituted-9,9'-bisacridinium salt and N,N-disubstituted carboxylic amide compound as the essential ingredients of Chemiluminescent Reagent II are the same as those for Chemiluminescent Reagent I. On the other hand, the aminoalcohol compound is shown by the general formula (3):

$$(HOR)_m NH_{3-m} \quad (3)$$

In the general formula (3), R is a divalent aliphatic hydrocarbon group having a carbon number of 1 to 5, and m is an integer of 1 to 3.

More concretely, the aminoalcohol compounds include, but not limited to, monoethanolamine, diethanolamine, triethanolamine, monoisopropanolamine, diisopropanolamine and triisopropanolamine.

Chemiluminescent Reagent II, which is obtained by further incorporating the aminoalcohol compound into Chemiluminescent Reagent II, has a lower blank level for the luminescence reaction, and realizes the chemluminescence reaction stably over a wider peroxidase concentration range.

The function of the aminoalcohol compound is not fully understood. It is however considered that the compound is involved in the charge transfer to the acridine ring from the counter ion of the bisacridinium salt, to accelerate its reaction, and, at the same time, further stabilizes the radicals of the charge-transferring complex formed to prevent the reaction with dissolved oxygen during the luminescence reaction and eliminate the causes for increasing the blank level, thereby realizing the stable high-sensitivity measurement of low blank level.

The molar ratios of the N,N-disubstituted carboxylic amide compound and the aminoalcohol compound to the charge-transferring complex of N,N'-disubstituted-9,9'-bisacridinium salt for Chemiluminescent Reagent II are 1 to 10,000, preferably 1 to 5,000, and 1 to 10,000, preferably 1 to 2,000, respectively.

Next, the method for producing the chemiluminescent reagent of the present invention, containing the charge-transferring complex of N,N'-disubstituted-9,9'-bisacridinium salt, is described.

Chemiluminescent Reagent I can be produced by irradiating an N,N'-disubstituted-9,9'-bisacridinium salt with light in the presence of an N,N-disubstituted carboxylic amide compound in a molar ratio of 1 to 10,000 to the above salt. On the other hand, Chemiluminescent Reagent II can be produced by irradiating a mixture of N,N'-disubstituted-9,9'-bisacridinium salt and N,N-disubstituted carboxylic amide compound with light, wherein an aminoalcohol compound is added to the reaction system during and/or after the charge-transfer reaction.

The N,N'-disubstituted-9,9'-bisacridinium salt used for producing the chemiluminescent reagent of the present invention is shown by the general formula (1A):

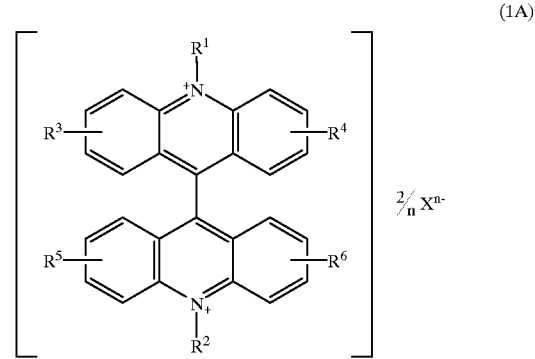

In the general formula (1A), $R^1$ and $R^2$ are each selected from the group consisting of an alkyl, aryl and halogenated aryl groups, and may be the same or different. Each of the alkyl, aryl and halogenated aryl group has a carbon number of 1 to 20, preferably 1 to 10 in the case of the alkyl group. The preferable alkyl groups include a straight-chain and branched methyl, ethyl, propyl, butyl, pentyl, hexyl, heptyl, octyl, nonyl and decyl groups. The preferable aryl groups are those having a carbon number of 6 to 20, including phenyl, tolyl and xylyl groups. They may be substituted by an alkyl group. Phenyl group is more preferable. The preferable halogenated aryl groups include halogenated phenyl, tolyl and xylyl groups, of which chlorophenyl group is more preferable.

In the general formula (1A), $R^3$, $R^4$, $R^5$ and $R^6$ are each selected from the group consisting of hydrogen, alkyl, aryl, alkoxy and aryloxy groups and haolgen, and may be the same or different. These hydrocarbon groups have a carbon number of 1 to 20, preferably 1 to 10. More concretely, these include a straight-chain or branched alkyl and alkoxy groups having a carbon number of 1 to 20, and an aryl and aryloxy group having a carbon number of 6 to 20, where the aryl and aryloxy group may be substituted with an alkyl group.

The preferred embodiments have an alkyl group having a carbon number of 1 to 10, or an aryl or halogenated aryl groups having a carbon number of 6 to 20 for each of $R^1$ and $R^2$, and hydrogen atom for each of $R^3$, $R^4$, $R^5$ and $R^6$.

In the general formula (1A), $X^{n-}$ is an n-valent anion; and n is 1 or 2. The anions include, but not limited to, chlorine, bromine, iodine, nitrate, carbonate, sulfate, phosphate and carbonate ions, of which nitrate ion is preferable.

More concretely, the N,N'-disubstituted-9,9'-bisacridinium salts include, but of course not limited to, N,N'-dimethyl-9,9'-bisacridinium, N,N'-diethyl-9,9'-bisacridinium, N,N'-dipropyl-9,9'-bisacridinium, N,N'-diisopropyl-9,9'-bisacridinium, N,N'-dibutyl-9,9'-bisacridinium, N,N'-diisobutyl-9,9'-bisacridinium, N,N'-diphenyl-9,9'-bisacridinium, and N,N'-di-m-chlorophenyl-9,9'-bisacridinium salts, of which N,N'-dimethyl-9,9'-bisacridinium dinitrate (Lucigenin) is preferable.

The N,N-disubstituted carboxylic amide compound, which may be the same as that described earlier, is shown by the general formula (2):

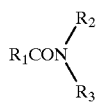

(2)

In the general formula (2), $R_1$ is selected from the group consisting of hydrogen, an alkyl group having a carbon number of 1 to 10, an alkenyl group having a carbon number of 2 to 10 and an aryl group having a carbon number of 6 to 20, wherein the aryl group may be substituted with a group selected from the group consisting of an alkyl, nitro, hydroxyl and amino groups, halogen and the like; $R_2$ is selected from the group consisting of methyl and ethyl groups; and $R_3$ is selected from the group consisting of an alkyl group having a carbon number of 1 to 10, an alkenyl group having a carbon number of 2 to 10 and an aryl group having a carbon number of 6 to 20, wherein the aryl group may be substituted with a group selected from the group consisting of alkyl, nitro, hydroxyl or amino group, halogen and the like. The alkyl groups for $R_1$ and $R_3$ include a straight-chain and branched methyl, ethyl, propyl, butyl, pentyl, hexyl, heptyl, octyl, nonyl and decyl groups. $R_1$ and $R_3$ may be bonded to each other to form a ring together with the carbon atom and nitrogen atom which are in the carbonyl and amide groups, respectively, to which each of $R_1$ and $R_3$ are bonded.

More concretely, the N,N-disubstituted carboxylic amide compounds include, but not limited to, N,N-dimethylformamide, N,N-dimethylacetoamide, N,N-dimethylacrylamide, N,N-dimethylpropionamide, N,N-dimethylbenzamide and N-methyl-2-pyrrolidone.

The aminoalcohol compound described earlier is shown by the general formula (3):

$$(HOR)_m NH_{3-m}$$ (3)

In the general formula (3), R is a divalent aliphatic hydrocarbon group having a carbon number of 1 to 5, and m is an integer of 1 to 3.

More concretely, the aminoalcohol compounds include, but not limited to, monoethanolamine, diethanolamine, triethanolamine, monoisopropanolamine, diisopropanolamine and triisopropanolamine.

For production of the chemiluminescent reagent of the present invention, an N,N'-disubstituted-9,9'-bisacridinium salt is irradiated with light in the presence of N,N-disubstituted carboxylic amide compound, wherein the light has a wavelength of approximately 290 nm to 800 nm (ultraviolet to visible region), preferably approximately 400 nm to 800 nm (visible region). The light sources include, but not limited to, high-voltage mercury, low-voltage mercury, bactericidal, fluorescent and white heat lamps, of which a white heat lamp is preferable.

The aminoalcohol compound may be added to the mixture of N,N'-disubstituted-9,9'-bisacridinium salt and N,N-disubstituted carboxylic amide compound before it is irradiated with light. However, it is recommended to add the compound during and/or after the charge-transfer reaction of the N,N'-disubstituted-9,9'-bisacridinium salt, accelerated in the presence of light. It is more preferable to add it after irradiation of light is stopped (i.e., after the charge-transfer reaction), viewed from keeping the luminescent performance stable.

Addition of the aminoalcohol compound to the chemiluminescent reagent of the present invention brings about the favorable effects of decreasing its blank level during the luminescence reaction process, increasing its luminescence intensity in a high peroxidase concentration range, and improving its preservation stability to prevent deterioration of its luminescent capacity while it is stored, thus greatly contributing to improvement of its performance, e.g., sensitivity and stability.

The chemiluminescent reagent of the present invention, having the above composition, is characterized by chemiluminescence it produces, extent of which depends on peroxidase concentration, under a basic condition (pH 7.5 to 13) in the presence of an excessive quantity of hydrogen peroxide.

The chemiluminescent reagent of the present invention, having the above luminescent characteristics, can be used for measuring peroxidase activity. These characteristics also make the reagent useful for enzyme immunoassay. These are described below.

Method for Measuring Peroxidase Activity

The present invention provides a method for measuring peroxidase activity, based on the chemiluminescent analysis for peroxidase's enzyme activity using the above chemiluminescent reagent in the presence of a hydrogen acceptor.

The present invention also provides a method for measuring peroxidase activity, based on the chemiluminescent analysis for peroxidase's enzyme activity using the above chemiluminescent reagent in the presence of a hydrogen acceptor, where a phenolic compound is used as the luminescent promoter.

The procedure for the measurement of peroxidase activity is not limited. In general, it prepares a mixture of chemiluminescent reagent solution, luminescent promoter and peroxidase enzyme as the sample, and adds a hydrogen acceptor solution to the above mixture in a specific basic pH range for chemiluminescence, extent of which is determined by an analyzer.

In the measurement of peroxidase activity, the chemiluminescent reagent is used at a concentration of $10^{-8}$ to 1 M, preferably $10^{-6}$ to $10^{-2}$ M, and its quantity is 10 to 500 μL, preferably 50 to 300 μL.

The chemiluminescent reagent of the present invention produces luminescence under a specific basic condition, extent of which is known to be intensified in the presence of luminescent promoter, such as a phenolic compound. The phenolic compounds useful for the present invention include, but not limited to, p-hydroxycinnamic acid, p-phenylphenol, p-(4-chlorophenyl)phenol, p-(4-bromophenyl) phenol, p-(4-iodophenyl)phenol, p-iodophenol, p-bromohenol, p-chlorophenol, 2,4-dichlorophenol, p-cumaric acid, 6-hydroxybenzothiazole, 2-naphthol and firefly luciferin. Of these, p-iodophenol, p-phenylphenol and 6-hydroxybenzothiazole are preferable. Quantity of the luminescent promoter is 0.01 to 100 molar times of the chemiluminescent reagent, preferably 0.1 to 10 times, and its concentration is $10^{-6}$ to 1 M, preferably $10^{-4}$ to $10^{-2}$ M.

The hydrogen acceptor for the present invention is not limited, so long as it can become the substrate for peroxidase enzyme. Although it can be an inorganic or organic peroxide, hydrogen peroxide is particularly preferable. It is necessary to use the hydrogen acceptor in sufficiently excess of the chemiluminescent reagent, 3 to 10,000 molar times, preferably 10 to 1,000 times.

In the measurement of peroxidase activity by the present invention, use of peroxidase as the maker allows to quantitatively analyze a variety of substances, e.g., antigen, antibody and nucleic acid. The peroxidase as the marker is not limited, and one of the preferable ones is horseradish peroxidase (HRP).

The basic buffer solution useful for the chemiluminescence is not limited. The useful ones include tris butter solution, phosphate butter solution, borate butter solution, carbonate butter solution and glycin/sodium hydroxide buffer solutions. The buffer solution is preferably used at a concentration of 1 mM to 1 M.

Moreover, a surfactant, chelating agent or the like may be used optionally for the reaction.

Chemiluminescence may be analyzed by, e.g., a luminometer, various photo-counters, X-ray film and other photosensitive films.

Method for Chemiluminescent Enzyme Immunoassay

The present invention also provides a method for chemiluminescent enzyme immunoassay for antigen or antibody with peroxidase enzyme as the marker, as one of the application of the novel chemiluminescent reagent of the present invention.

The method for chemiluminescent enzyme immunoassay using the chemiluminescent reagent of the present invention comprises two steps; (1) immuno-reaction step, in which an antibody or antigen marked with peroxidase enzyme is mixed with and captured by an antigen, antibody or agglomerate thereof in the sample to be analyzed by the antigen-antibody reaction, to form the immune complex marked with the peroxidase enzyme, and (2) chemiluminescent reaction step, in which the immune complex is analyzed by the chemiluminescent method which follows the marker enzyme present in its molecule.

The procedure of the antigen-antibody reaction for the above step (1) is not limited, so long as it can use the chemiluminescent reagent of the present invention. Some of useful procedures are described below.

(1) Sandwich method, in which an antigen to be analyzed in the sample is captured by an antibody bound to an insoluble carrier, and then is reacted with an antibody marked with peroxidase, (2) two-antibody method, which is the sandwich method in which an antibody from an animal species different from that for the antibody bound to an insoluble carrier is reacted, after being marked, with the sandwich complex, (3) competition method, in which an antibody bound to an insoluble carrier is reacted with an antigen to be analyzed in the sample in the presence of an antigen marked with peroxidase.

(4) coagulating sedimentation, in which a marked antibody or antigen, which shows a peculiar reaction with another antigen or antibody to be analyzed, is acted on the sample to cause coagulating sedimentation, and the sediment is centrifugally treated, to measure the marker in the separated immune complex, (5) antibody detection, in which an antibody to be analyzed in the sample (antihuman gamma globlin antibody marked with peroxidase enzyme) is acted on an antigen bound to an insoluble carrier, and (6) biotin-avidin method, in which an antibody marked with biotin is reacted with avidin marked with peroxidase enzyme.

The insoluble carriers useful for the chemiluminescent enzyme immunoassay of the present invention include those of polymer compounds, e.g., polystyrene, polyethylene, polypropylene, polyester, polyacrylonitrile, fluorine resin, cross-linked dextran and polysaccharide; and those of others, e.g., glass, metals, magnetic particles and a combination thereof. The insoluble carrier can take various shapes, e.g., tray, spherical, fibrous, rod, disk, container, cell, micro plate and test tube shapes. The method for immobilizing the antigen or antibody on the insoluble carrier is not limited. For example, it can be immobilized by physical adsorption, covalent bonding and ionic bonding.

The antibody useful for the chemiluminescent enzyme immunoassay of the present invention may be monoclonal or polyclonal. It may be in the shape of whole body or fragment, e.g., F(ab')$_2$ or Fab. The origin for the antibody is not limited. The preferable ones include those from mouse, rat, rabbit, sheep, goat and fowl.

The chemiluminescent reaction as the second step for the chemiluminescent enzyme immunoassay of the present invention analyzes activity of peroxidase as the marker captured by an insoluble carrier by the action of hydrogen acceptor using the above chemiluminescent reagent in the presence of a luminescent promoter. This procedure is not limited. One of the common methods adds, at a specific basic pH level, a hydrogen acceptor (e.g., aqueous solution of hydrogen peroxide) to the sample reagent containing a chemiluminescent material or luminescent promoter, immunologically captured by an insoluble carrier, to produce the chemiluminescence, extent of which is determined by an adequate analyzer.

In the chemiluminescent enzyme immunoassay of the present invention, the chemiluminescent reagent produces luminescence at pH 7.5 to 13, extent of which is known to be intensified in the presence of luminescent promoter, such as a phenolic compound. The chemiluminescent reagent is used at a concentration of $10^{-8}$ to 1 M, preferably $10^{-6}$ to $10^{-2}$ M, and its quantity is 10 to 500 µL, preferably 50 to 300 µL. Quantity of the luminescent promoter is 0.01 to 100 molar times of the chemiluminescent reagent, preferably 0.1 to 10 times. The same hydrogen acceptor, peroxidase and basic buffer solution as used for the measurement of peroxidase activity may be used under the same conditions.

EFFECTS OF INVENTION

The novel chemiluminescent reagent of the present invention provides can be easily produced from an inexpensive stock in a relatively short time. It produces chemiluminescence in the presence of hydrogen peroxide and peroxidase, extent of which depends on peroxidase concentration, a property which can be used to detect peroxidase enzyme at a high sensitivity. Use of an antigen, antibody, nucleic acid or the like marked with peroxidase allows to measure, peculiarly and at a high sensitivity, an antigen, antibody or the like by the enzyme immunoassay, protein by the western blotting method, DNA and RNA by the southern or northern blotting method, and nucleic acid by the method which uses an enzyme-marked nucleic acid probe.

EXAMPLES

The present invention is described more concretely by EXAMPLES and COMPARATIVE EXAMPLES, which by no means limit the present invention.

The luminometer used to determine luminescence in EXAMPLES and COMPARATIVE EXAMPLES is LUMINOUS CT-9000D manufactured by DIA-IATRON CO., LTD.

Example 1
Preparation of Chemiluminescent Reagent Containing a Charge-transferring Complex of N,N'-dimethyl-9,9'-bisacridinium Dihydroiodide Salt and N,N'-dimethylacetoamide A mixture of a $1\times10^{-2}$ mol/L aqueous solution of lucigenin and solid potassium iodide (molar ratio: 1:2) was stirred at room temperature for 1 hour, to produce a red precipitate. The precipitate-containing reaction solution was put in an eggplant-shaped flask and heated by a rotary evaporator at 60° C. under a vacuum to distill off water serving as the solvent. The residuum of the solidified red precipitate was washed with benzene to remove by-products, and the benzene-insolubles were separated by filtration and dried, to produce the raw product. The raw product was dissolved in a small quantity of water by heating at 95° C. in a water bath, while light was shielded. It was cooled back to room temperature, and then kept at 4° C. The resultant precipitate was separated by filtration and dried, and unreacted substances were removed, to produce the N,N'-dimethyl-9,9'-bisacridinium dihydroiodide salt in a yield of approximately 70%. 1.5 mg of this compound, put in a test tube, was dissolved in 1 mL of N,N-dimethylacetoamide, and the solution was irradiated with light from a 250 W copy lamp for 7 hours while the test tube was held in a water bath kept at 30° C., to prepare the chemiluminescent reagent containing a charge-transferring complex of N,N'-dimethyl-9,9'-bisacridinium dihydroiodide salt. Formation of the charge-transferring complex was confirmed by a spectrophotometer, as evidenced by emergence of a broad absorption band with a maximum at around 550 nm in the ultraviolet absorption spectral pattern.

(Evaluation of chemiluminescent reagent performance)

Performance of the chemiluminescent reagent prepared above was evaluated by its peroxidase activity.

A mixture of 50 µL of the chemiluminescent reagent and 2.95 mL of a 0.1 M trishydrochloric acid buffer solution (pH: 7.8) was prepared. This solution was then incorporated with 100 µL of a 0.1 M trishydrochloric acid buffer solution (pH: 7.8) containing 10 mM of p-iodophenol, to prepare the chemiluminescent reagent solution. Each of a plurality of wells supported by a micro plate for chemiluminescence measurement was charged with a 0.1 M trishydrochloric acid buffer solution (pH: 7.8) containing a varying concentration of horseradish peroxidase (HRP). The chemiluminescent solution and 100 µL of a 0.0017% aqueous solution of hydrogen peroxide were charged to the wells one by one to produce the chemiluminescence, extent of which was added up for 0 to 5 sec by a luminometer. Table 1 gives a range of luminescent intensity corresponding to HRP concentration. It is thus confirmed that peroxidase activity can be determined at an HRP concentration of up to $1\times10^{-13}$ mol/L.

Therefore, it is found that extent of luminescence can be controlled by peroxidase concentration, to a very low level of the concentration.

Example 1-1
Measurement of Peroxidase Activity

Each of a plurality of wells supported by a micro plate for chemiluminescence measurement was charged with 100 µL of a 0.1 M trishydrochloric acid buffer solution (pH: 7.8) containing a varying concentration of horseradish peroxidase (HRP), 800 µL of a 10 mM p-iodophenol solution, and 100 µL of the chemiluminescent reagent solution (20 µL of the chemiluminescent reagent prepared by EXAMPLE 1 dissolved in 9.18 mL of a 10 mM trishydrochloric acid buffer solution (pH: 7.8)), to which 50 µL of a 0.0034% aqueous solution of hydrogen peroxide was added, to produce the chemiluminescence. Extent of the chemiluminescence was added up for 1 to 5 sec by a luminometer, to determine luminescent intensity, shown in Table A. It is thus confirmed that HRP concentration can be measured up to $1\times10^{-19}$ mol/assay.

TABLE A

| HRP (mol/assay) | Luminescence |
|---|---|
| 0 | 119 |
| $5 \times 10^{-20}$ | 191 |
| $1 \times 10^{-19}$ | 256 |
| $1 \times 10^{-18}$ | 2195 |
| $1 \times 10^{-17}$ | 16453 |
| $1 \times 10^{-16}$ | 109868 |
| $1 \times 10^{-15}$ | 955491 |
| $1 \times 10^{-14}$ | 3177943 |

Example 1-2
Measurement of α-fetoprotein (AFP) by the Simultaneous Sandwich CLEIA Method Using the Chemiluminescent Reagent Prepared by EXAMPLE 1

50 µL of a PBS solution (pH: 7.4) containing 2% BSA which contained 0 to 800 ng/mL of purified human AFP (standard material) and 100 µL of a PBS solution (pH: 7.4) containing 2% BSA which contained approximately 3 µg/mL of mouse antihuman AFP monoclonal antibody marked with the peroxidase enzyme prepared by REFERENCE EXAMPLE 2 were charged to wells supported by a micro plate, white in color, immobilizing the rabbit antihuman AFP polyclonal antibody prepared by REFERENCE EXAMPLE 1, and the mixture was incubated at 37° C. for 1 hour. The solution was removed from each well under a vacuum, and the well inside was washed with normal saline solution. Then, each well was charged with 100 µL of a 75 mM trishydrochloric acid buffer solution (pH: 7.8), 100 µL of the chemiluminescent reagent solution prepared by EXAMPLE 1, and 50 µL of a 75 mM trishydrochloric acid buffer solution (pH: 7.8) containing a 0.0017% aqueous solution of hydrogen peroxide, in this order, to produce the chemiluminescence, extent of which was added up for 1 to 5 sec by a luminometer, to determine chemiluminescent intensity. It was plotted against concentration of the standard material, to prepare the calibration curve (FIG. 1). As shown, the intensity is well correlated with the concentration. This calibration curve can be used to determine concentration of human AFP present in the human serum sample to 0.01 ng/mL.

Example 2
Preparation of Chemiluminescent Reagent Containing a Charge-transferring Complex of N,N'-dimethyl-9,9'- bisacridinium Dihydrochloride Salt and N,N'-dimethylacetoamide

A mixture of a $1\times10^{-2}$ mol/L aqueous solution of lucigenin and solid potassium chloride (molar ratio: 1:2) was stirred at room temperature for 1 hour, to produce a brownish red precipitate. The precipitate-containing reaction solution was put in an eggplant-shaped flask and heated by a rotary evaporator at 60° C. under a vacuum to distill off water serving as the solvent. The residuum of the solidified brownish red precipitate was washed with benzene to remove by-products, and the benzene-insolubles were separated by filtration and dried, to produce the raw product. The raw product was dissolved in a small quantity of water by heating at 95° C. in a water bath, while light was shielded. It was cooled back to room temperature, and then kept at 4° C. The resultant precipitate was separated by filtration and dried, and unreacted substances were removed, to produce the N,N'-dimethyl-9,9'-bis-acridinium dihydrochloride salt in a yield of approximately 70%. 1.5 mg of this compound, put in a test tube, was dissolved in 1 mL of N,N-dimethylacetoamide, and the solution was irradiated with light from a 250 W copy lamp for 7 hours while the test tube was held in a water bath kept at 30° C., to prepare the chemiluminescent reagent containing a charge-transferring complex of N,N'-dimethyl-9,9'-bis-acridinium dihydrochloride salt.

(Evaluation of chemiluminescent reagent performance)

The same procedure as used for EXAMPLE 1, except the chemiluminescent reagent was replaced by the one prepared in EXAMPLE 2, was repeated under the same conditions, to measure its peroxidase activity. The results are given in Table 1. It is thus confirmed that peroxidase activity can be determined at a concentration of up to $1\times10^{-13}$ mol/L, and that luminescence can be controlled by peroxidase concentration.

Example 3
Preparation of Chemiluminescent Reagent Containing a Charge-transferring Complex of N,N'-dimethyl-9,9'-bisacridinium Dinitrate Salt and N,N'-diethylacetoamide 1.5 mg of lucigenin was dissolved in 1 mL of N,N-dimethylacetoamide in a test tube, and the solution was irradiated with light from a 250 W copy lamp for 7 hours while the test tube was held in a water bath kept at 30° C., to prepare the chemiluminescent reagent containing a charge-transferring complex of N,N'-dimethyl-9,9'-bisacridinium dinitrate salt.

(Evaluation of chemiluminescent reagent performance)

The same procedure as used for EXAMPLE 1, except the chemiluminescent reagent was replaced by the one prepared in EXAMPLE 3, was repeated under the same conditions, to measure its peroxidase activity. The results are given in Table 1. It is thus confirmed that peroxidase activity can be determined at a concentration of up to $1\times10^{-13}$ mol/L, and that luminescence can be controlled by peroxidase concentration.

Example 3-1
Measurement of Peroxidase Activity

Each of a plurality of wells supported by a micro plate for chemiluminescence measurement was charged with 100 µL of a 0.1 M trishydrochloric acid buffer solution (pH: 7.8) containing a varying concentration of horseradish peroxidase (HRP), 800 µL of a 10 mM p-iodophenol solution, and 100 µL of the chemiluminescent reagent solution (20 µL of the chemiluminescent reagent prepared by EXAMPLE 3 dissolved in 9.18 mL of a 10 mM trishydrochloric acid buffer solution (pH: 7.8)), to which 50 µL of a 0.0034% aqueous solution of hydrogen peroxide was added, to produce the chemiluminescence. Extent of the chemiluminescence was added up for 1 to 5 sec by a luminometer, to determine luminescent intensity, shown in Table B. It is thus confirmed that HRP concentration can be measured up to $1\times10^{-19}$ mol/assay.

TABLE B

| HRP (mol/assay) | Luminescence |
| --- | --- |
| 0 | 131 |
| $5 \times 10^{-20}$ | 203 |
| $1 \times 10^{-19}$ | 281 |
| $1 \times 10^{-18}$ | 2587 |
| $1 \times 10^{-17}$ | 21578 |
| $1 \times 10^{-16}$ | 165711 |
| $1 \times 10^{-15}$ | 997519 |
| $1 \times 10^{-14}$ | 2965678 |

Example 3-2
Measurement of β Chain of Human Chorionic Gonadotrophin (βhCG) by the Simultaneous Sandwich CLEIA Method Using the Chemiluminescent Reagent Prepared by EXAMPLE 3

Figure 2:
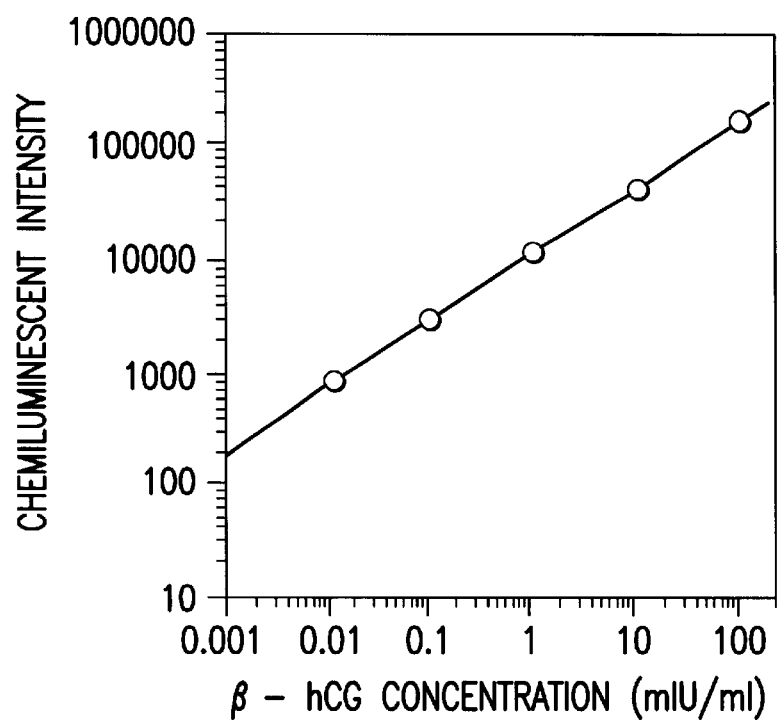
FIG. 2 is a calibration curve for measuring β chain of human chorionic gonadotrophin (βhCG) as the standard, plotting chemiluminescence intensity of the reaction system of EXAMPLE 3-2 against concentration of βhCG.

50 µL of a PBS solution (pH: 7.4) containing 2% BSA which contained 0 to 100 mIU/mL of purified βhCG (standard material) and 100 µL of a PBS solution (pH: 7.4) containing 2% BSA which contained approximately 2 µg/mL of mouse anti-βhCG monoclonal antibody marked with the peroxidase enzyme prepared by REFERENCE EXAMPLE 2 were charged to wells supported by a micro plate, white in color, immobilizing the rabbit antihuman βhCG polyclonal antibody prepared by REFERENCE EXAMPLE 1, and the mixture was incubated at 37° C. for 1 hour. The solution was removed from each well under a vacuum, and the well inside was washed with normal saline solution. Then, each well was charged with 100 µL of a 75 mM trishydrochloric acid buffer solution (pH: 7.8), 100 µL of the chemiluminescent reagent solution prepared by EXAMPLE 3, and 50 µL of a 75 mM trishydrochloric acid buffer solution (pH: 7.8) containing a 0.0017% aqueous solution of hydrogen peroxide, in this order, to produce the chemiluminescence, extent of which was added up for 1 to 5 sec by a luminometer, to determine chemiluminescent intensity. It was plotted against concentration of the standard material, to prepare the calibration curve (FIG. 2). As shown, the intensity is well correlated with the concentration. This calibration curve can be used to determine concentration of βhCG present in the human serum sample to 0.01 mIU/mL.

Example 4
Preparation of Chemiluminescent Reagent Containing a Charge-transferring Complex of N,N'-dimethyl-9,9'-bisacridinium Dihydroiodide Salt, and N,N'-dimethylacetoamide and Triethanolamine A mixture of a $1\times10^{-2}$ mol/L aqueous solution of lucigenin and solid potassium iodide (molar ratio: 1:2) was stirred at room temperature for 1 hour, to produce a red precipitate. The precipitate-containing reaction solution was put in an eggplant-shaped flask and heated by a rotary evaporator at 60° C. under a vacuum to distill off water serving as the solvent. The residuum of the solidified red precipitate was washed with benzene to remove by-products, and the benzene-insolubles were separated by filtration and dried, to produce the raw product. The raw product was dissolved in a small quantity of water by heating at 95° C. in a water bath, while light was shielded. It was cooled back to room temperature, and then kept at 4° C. The resultant precipitate was separated by filtration and dried, and unreacted substances were removed, to produce the N,N'-dimethyl-9,9'-bisacridinium dihydroiodide salt in a yield of approximately 70%. 1.5 mg of this compound, put in a test tube, was dissolved in 1 mL of N,N-dimethylacetoamide, and the solution was irradiated with light from a 250 W copy lamp for 7 hours while the test tube was held in a water bath kept at 30° C. and then incorporated with 0.5 mL of triethanolamine, to prepare the chemiluminescent reagent containing a charge-transferring complex of N,N'-dimethyl-9,9'-bisacridinium dihydroiodide salt.

(Evaluation of chemiluminescent reagent performance)

The same procedure as used for EXAMPLE 1, except the chemiluminescent reagent was replaced by the one prepared in EXAMPLE 4, was repeated under the same conditions, to measure its peroxidase activity. The results are given in Table 1. It is thus confirmed that peroxidase activity can be determined at a concentration of up to $1\times10^{-13}$ mol/L, and that luminescence can be controlled by peroxidase concentration.

Example 4-1

Measurement of Peroxidase Activity

Each of a plurality of wells supported by a micro plate for chemiluminescence measurement was charged with 100 µL of a 0.1 M trishydrochloric acid buffer solution (pH: 7.8) containing a varying concentration of horseradish peroxidase (HRP), 800 µL of a 10 mM p-iodophenol solution, and 100 µL of the chemiluminescent reagent solution (20 µL of the chemiluminescent reagent prepared by EXAMPLE 4 dissolved in 9.18 mL of a 10 mM trishydrochloric acid buffer solution (pH: 7.8)), to which 50 µL of a 0.0034% aqueous solution of hydrogen peroxide was added, to produce the chemiluminescence. Extent of the chemiluminescence was added up for 1 to 5 sec by a luminometer, to determine luminescent intensity, shown in Table C. It is thus confirmed that HRP concentration can be measured up to $1\times10^{-19}$ mol/assay.

TABLE C

| HRP (mol/assay) | Luminescence |
|---|---|
| 0 | 51 |
| $5\times10^{-20}$ | 97 |
| $1\times10^{-19}$ | 114 |
| $1\times10^{-18}$ | 928 |
| $1\times10^{-17}$ | 7469 |
| $1\times10^{-16}$ | 59344 |
| $1\times10^{-15}$ | 479751 |
| $1\times10^{-14}$ | 3865678 |

Example 4-2

Measurement of Human Prolactin (PRL) by the Simultaneous Sandwich CLEIA Method Using the Chemiluminescent Reagent Prepared by EXAMPLE 4

Figure 3:
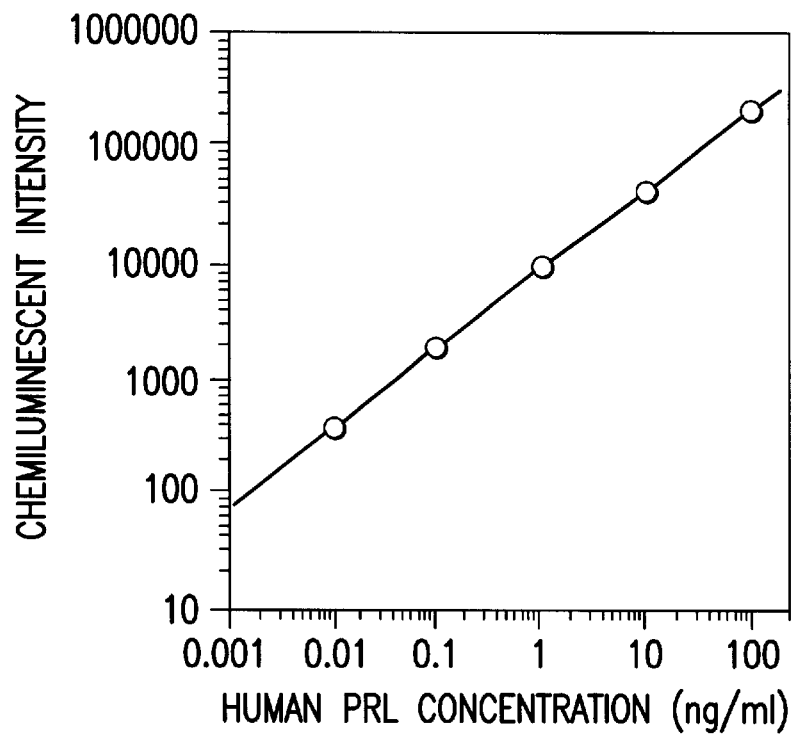
FIG. 3 is a calibration curve for measuring human prolactin (PRL) as the standard, plotting chemiluminescence intensity of the reaction system of EXAMPLE 4-2 against concentration of human PRL.

50 µL of a PBS solution (pH: 7.4) containing 2% BSA which contained 0 to 100 ng/mL of purified human PRL (standard material) and 100 µL of a PBS solution (pH: 7.4) containing 2% BSA which contained approximately 3 µg/mL of mouse antihuman PRL monoclonal antibody marked with the peroxidase enzyme prepared by REFERENCE EXAMPLE 2 were charged to wells supported by a micro plate, white in color, immobilizing the rabbit antihuman PRL polyclonal antibody prepared by REFERENCE EXAMPLE 1, and the mixture was incubated at 37° C. for 1 hour. The solution was removed from each well under a vacuum, and the well inside was washed with normal saline solution. Then, each well was charged with 100 µL of a 75 mM trishydrochloric acid buffer solution (pH: 7.8), 100 µL of the chemiluminescent reagent solution prepared by EXAMPLE 4, and 50 µL of a 75 mM trishydrochloric acid buffer solution (pH: 7.8) containing a 0.0017% aqueous solution of hydrogen peroxide, in this order, to produce the chemiluminescence, extent of which was added up for 1 to 5 sec by a luminometer, to determine chemiluminescent intensity. It was plotted against concentration of the standard material, to prepare the calibration curve (FIG. 3). As shown, the intensity is well correlated with the concentration. This calibration curve can be used to determine concentration of human PRL present in the human serum sample to 0.01 ng/mL.

Example 5

Preparation of Chemiluminescent Reagent Containing a Charge-transferring Complex of N,N'-dimethyl-9,9'-bisacridinium Dinitrate Salt, and N,N'-dimethylacetoamide and Triethanolamine 1.5 mg of lucigenin was dissolved in 1 mL of N,N-dimethylacetoamide in a test tube, and the solution was irradiated with light from a 250 W copy lamp for 7 hours while the test tube was held in a water bath kept at 30° C. and then incorporated with 0.5 mL of triethanolamine, to prepare the chemiluminescent reagent.

(Evaluation of chemiluminescent reagent performance)

The same procedure as used for EXAMPLE 1, except the chemiluminescent reagent was replaced by the one prepared in EXAMPLE 5, was repeated under the same conditions, to measure its peroxidase activity. The results are given in Table 1. It is thus confirmed that peroxidase activity can be determined at a concentration of up to $1\times10^{-13}$ mol/L, and that luminescence can be controlled by peroxidase concentration.

Example 5-1

Measurement of Peroxidase Activity

Each of a plurality of wells supported by a micro plate for chemiluminescence measurement was charged with 100 µL of a 0.1 M trishydrochloric acid buffer solution (pH: 7.8) containing a varying concentration of horseradish peroxidase (HRP), 800 µL of a 10 mM p-iodophenol solution, and 100 µL of the chemiluminescent reagent solution (20 µL of the chemiluminescent reagent prepared by EXAMPLE 5 dissolved in 9.18 mL of a 10 mM trishydrochloric acid buffer solution (pH: 7.8)), to which 50 µL of a 0.0034% aqueous solution of hydrogen peroxide was added, to produce the chemiluminescence. Extent of the chemiluminescence was added up for 1 to 5 sec by a luminometer, to determine luminescent intensity, shown in Table D. It is thus confirmed that HRP concentration can be measured up to $1\times10^{-19}$ mol/assay.

TABLE D

| HRP (mol/assay) | Luminescence |
|---|---|
| 0 | 48 |
| $5\times10^{-20}$ | 76 |
| $1\times10^{-19}$ | 112 |
| $1\times10^{-18}$ | 895 |
| $1\times10^{-17}$ | 7165 |
| $1\times10^{-16}$ | 57293 |

TABLE D-continued

| HRP (mol/assay) | Luminescence |
|---|---|
| $1 \times 10^{-15}$ | 366592 |
| $1 \times 10^{-14}$ | 2944398 |

Example 5-2
Measurement of α-fetoprotein (AFP) by the Simultaneous Sandwich CLEIA Method Using the Chemiluminescent Reagent Prepared by EXAMPLE 5

Figure 4:
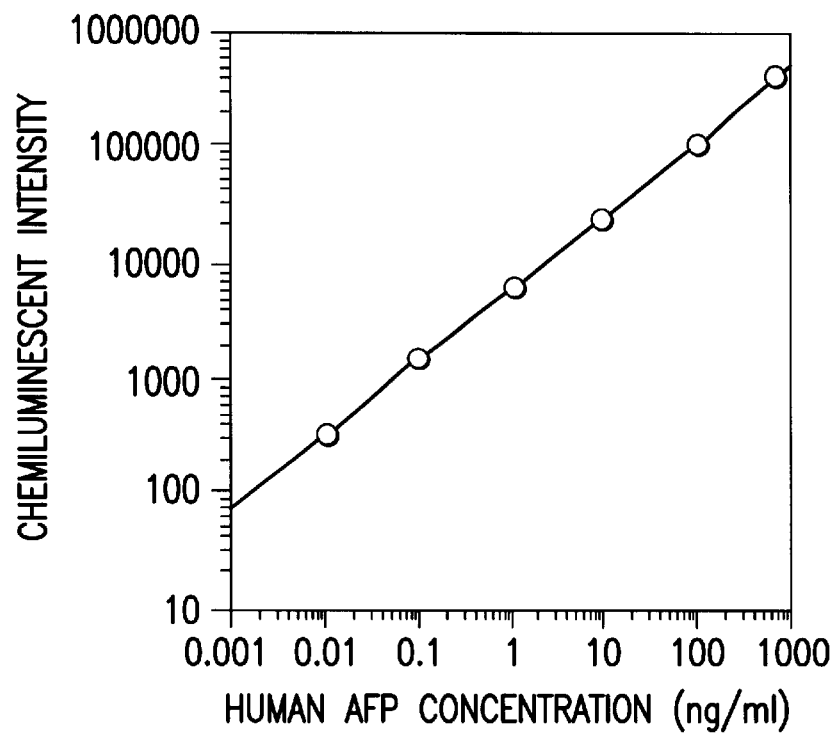
FIG. 4 is a calibration curve for measuring human αAFT as the standard, plotting chemiluminescence intensity of the reaction system of EXAMPLE 5-2 against concentration of human αAFT.

50 µL of a PBS solution (pH: 7.4) containing 2% BSA which contained 0 to 800 ng/mL of purified human AFP (standard material) and 100 µL of a PBS solution (pH: 7.4) containing 2% BSA which contained approximately 3 µg/mL of mouse antihuman AFP monoclonal antibody marked with the peroxidase enzyme prepared by REFERENCE EXAMPLE 2 were charged to wells supported by a micro plate, white in color, immobilizing the rabbit antihuman AFP polyclonal antibody prepared by REFERENCE EXAMPLE 1, and the mixture was incubated at 37° C. for 1 hour. The solution was removed from each well under a vacuum, and the well inside was washed with normal saline solution. Then, each well was charged with 100 µL of a 75 mM trishydrochloric acid buffer solution (pH: 7.8), 100 µL of the chemiluminescent reagent solution prepared by EXAMPLE 5, and 50 µL of a 75 mM trishydrochloric acid buffer solution (pH: 7.8) containing a 0.0017% aqueous solution of hydrogen peroxide, in this order, to produce the chemiluminescence, extent of which was added up for 1 to 5 sec by a luminometer, to determine chemiluminescent intensity. It was plotted against concentration of the standard material, to prepare the calibration curve (FIG. 4). As shown, the intensity is well correlated with the concentration. This calibration curve can be used to determine concentration of human AFP present in the human serum sample to 0.01 ng/mL.

Example 6
Preparation of Chemiluminescent Reagent 1.5 mg of lucigenin was dissolved in 1 mL of N,N-dimethylformamide in a test tube, and the solution was irradiated with light from a 250 W copy lamp for 5 hours while the test tube was held in a water bath kept at 30° C., to prepare the chemiluminescent reagent containing the chemiluminescent substance.

(Evaluation of chemiluminescent reagent performance)

The same procedure as used for EXAMPLE 1, except the chemiluminescent reagent was replaced by the one prepared in EXAMPLE 6, was repeated under the same conditions, to measure its peroxidase activity. The results are given in Table 1. Luminescent intensity shown in Table 1 is higher than that given by the reagent prepared by COMPARATIVE EXAMPLE 2 in the absence of light irradiation, indicating that light irradiation improves luminescent intensity.

Example 6-1
Measurement of Peroxidase Activity

The chemiluminescent reagent prepared by EXAMPLE 6 was diluted 500 times with a 75 m M trishydrochloric acid buffer solution (pH: 8.0) containing $8 \times 10^{-4}$ M of p-iodophenol. Each of a plurality of wells supported by a micro plate for chemiluminescence measurement was charged with 100 µL of a 75 mM trishydrochloric acid buffer solution (pH: 8.0) containing a varying concentration of horseradish peroxidase (HRP), and then with 100 µL of the above chemiluminescent reagent solution and 50 µL of a 75 mM trishydrochloric acid buffer solution (pH: 8.0) containing a 0.0017% aqueous solution of hydrogen peroxide by solution injecting units, in this order, to produce the chemiluminescence. Extent of the chemiluminescence was added up for 0 to 5 sec by a luminometer, to determine luminescent intensity, shown in Table E. It is thus confirmed that HRP concentration can be measured up to $5 \times 10^{-19}$ mol/assay, and that both sensitivity and luminous intensity are improved from those given by the reagent prepared by COMPARATIVE EXAMPLE 2 in the absence of light irradiation.

TABLE E

| HRP (mol/assay) | Luminescence |
|---|---|
| 0 | 546 |
| $5 \times 10^{-19}$ | 793 |
| $1 \times 10^{-19}$ | 1241 |
| $1 \times 10^{-18}$ | 5541 |
| $1 \times 10^{-17}$ | 43431 |
| $1 \times 10^{-16}$ | 341837 |
| $1 \times 10^{-15}$ | 3168503 |

Example 7
Preparation of Chemiluminescent Reagent 1.5 mg of lucigenin was dissolved in 1 mL of N-methyl-2-pyrrolidone in a test tube, and the solution was irradiated with light from a 250 W copy lamp for 3 hours while the test tube was held in a water bath kept at 30° C, to prepare the chemiluminescent reagent containing the chemiluminescent substance.

(Evaluation of chemiluminescent reagent performance)

The same procedure as used for EXAMPLE 1, except the chemiluminescent reagent was replaced by the one prepared in EXAMPLE 7, was repeated under the same conditions, to measure its peroxidase activity. The results are given in Table 1. Luminescent intensity shown in Table 1 is higher than that given by the reagent prepared by COMPARATIVE EXAMPLE 3 in the absence of light irradiation, indicating that light irradiation improves luminescent intensity.

Example 7-1
Measurement of Peroxidase Activity

The chemiluminescent reagent prepared by EXAMPLE 7 was diluted 500 times with a 75 m M trishydrochloric acid buffer solution (pH: 8.0) containing $8 \times 10^{-4}$ M of p-iodophenol. Each of a plurality of wells supported by a micro plate for chemiluminescence measurement was charged with 100 µL of a 75 mM trishydrochloric acid buffer solution (pH: 8.0) containing a varying concentration of horseradish peroxidase (HRP), and then with 100 µL of the above chemiluminescent reagent solution and 50 µL of a 75 mM trishydrochloric acid buffer solution (pH:8.0) containing 0.0017% aqueous solution of hydrogen peroxide by solution injecting units, in this order, to produce the chemiluminescence. Extent of the chemiluminescence was added up for 0 to 5 sec by a luminometer, to determine luminescent intensity, shown in Table F. It is thus confirmed that HRP concentration can be measured up to $5 \times 10^{-19}$ mol/assay, and that both sensitivity and luminous intensity are improved from those given by the reagent prepared by COMPARATIVE EXAMPLE 3 in the absence of light irradiation.

TABLE F

| HRP (mol/assay) | Luminescence |
| --- | --- |
| 0 | 398 |
| $5 \times 10^{-19}$ | 542 |
| $1 \times 10^{-19}$ | 956 |
| $1 \times 10^{-18}$ | 2670 |
| $1 \times 10^{-17}$ | 18693 |
| $1 \times 10^{-16}$ | 261848 |
| $1 \times 10^{-15}$ | 2887914 |

Example 8
Preparation of Chemiluminescent Reagent 1.5 mg of lucigenin was dissolved in 1 mL of N,N-dimethylacetoamide in a test tube, and the solution was irradiated with light from a 250 W copy lamp for 7 hours while the test tube was held in a water bath kept at 30° C. and incorporated with 0.1 mL of monoethanolamine, to prepare the chemiluminescent reagent containing the chemiluminescent substance.

(Evaluation of chemiluminescent reagent performance)

The same procedure as used for EXAMPLE 1, except the chemiluminescent reagent was replaced by the one prepared in EXAMPLE 8, was repeated under the same conditions, to measure its peroxidase activity and evaluate its performance. The results are given in Table 1.

Example 8-1
Measurement of Peroxidase Activity

The same procedure as used for EXAMPLE 7-1, except the chemiluminescent reagent was replaced by the one prepared in EXAMPLE 8, was repeated under the same conditions, to measure its peroxidase activity. The results are given in Table G. It is thus confirmed that HRP concentration can be measured up to $1 \times 10^{-19}$ mol/assay, and that both sensitivity and luminous intensity are improved from those observed in COMPARATIVE EXAMPLES 6-1 and 7-1 which used no monoethanol amine.

TABLE G

| HRP (mol/assay) | Luminescence |
| --- | --- |
| 0 | 216 |
| $5 \times 10^{-20}$ | 379 |
| $1 \times 10^{-19}$ | 824 |
| $1 \times 10^{-18}$ | 6608 |
| $1 \times 10^{-17}$ | 79966 |
| $1 \times 10^{-16}$ | 1585325 |
| $1 \times 10^{-15}$ | 12371903 |

Comparative Example 1
Preparation of Chemiluminescent Reagent 1.5 mg of lucigenin was dissolved in 2 mL of N,N-dimethylacetoamide in a test tube, and the solution was allowed to stand at room temperature for 3 hours and incorporated with 2 mL of pure water, to prepare the chemiluminescent reagent.

(Evaluation of chemiluminescent reagent performance)

Each of a plurality of wells for chemiluminescence measurement was charged with 20 μL of the above chemiluminescent reagent immediately after it was prepared, and then with 200 μL of a 0.1 M trishydrochloric acid buffer solution (pH: 8.4) containing a varying concentration of horseradish peroxidase (HRP) and 20 μL of a 0.1 M trishydrochloric acid buffer solution (pH: 8.4) containing 10 mM of p-iodophenol, to which 50 μL of a 0.0034% aqueous solution of hydrogen peroxide was added, to produce the chemiluminescence, extent of which was added up for 0 to 5 sec by a luminometer, to determine luminescent intensity. Luminescent intensity is insufficient, as shown in Table 1.

Comparative Example 1-1
Measurement of Peroxidase Activity

100 μL of a 0.1 M trishydrochloric acid buffer solution (pH: 8.4) containing $4 \times 10^{-5}$ M of the chemiluminescent reagent prepared by COMPARATIVE EXAMPLE 1 and $10^{-3}$ M of p-iodophenol was mixed with 100 μL of a 0.1 M trishydrochloric acid buffer solution (pH: 8.4) containing a varying concentration of horseradish peroxidase (HRP), to which 50 μL of a 0.0034% aqueous solution of hydrogen peroxide was added, to produce the chemiluminescence. Extent of the chemiluminescence was added up for 0 to 5 sec by a luminometer, to determine luminescent intensity. The results are given in Table a. As shown, HRP concentration can be measured up to $1 \times 10^{-18}$ mol/assay.

TABLE a

| HRP (mol/assay) | Luminescence |
| --- | --- |
| 0 | 374 |
| $5 \times 10^{-19}$ | 425 |
| $1 \times 10^{-18}$ | 746 |
| $1 \times 10^{-17}$ | 2688 |
| $1 \times 10^{-16}$ | 33007 |
| $1 \times 10^{-15}$ | 109582 |
| $1 \times 10^{-14}$ | |

Comparative Example 1-2
Measurement of α-fetoprotein (AFP) by the Simultaneous Sandwich CLEIA Method Using the Chemiluminescent Reagent Prepared by COMPARATIVE EXAMPLE 1

Figure 6:
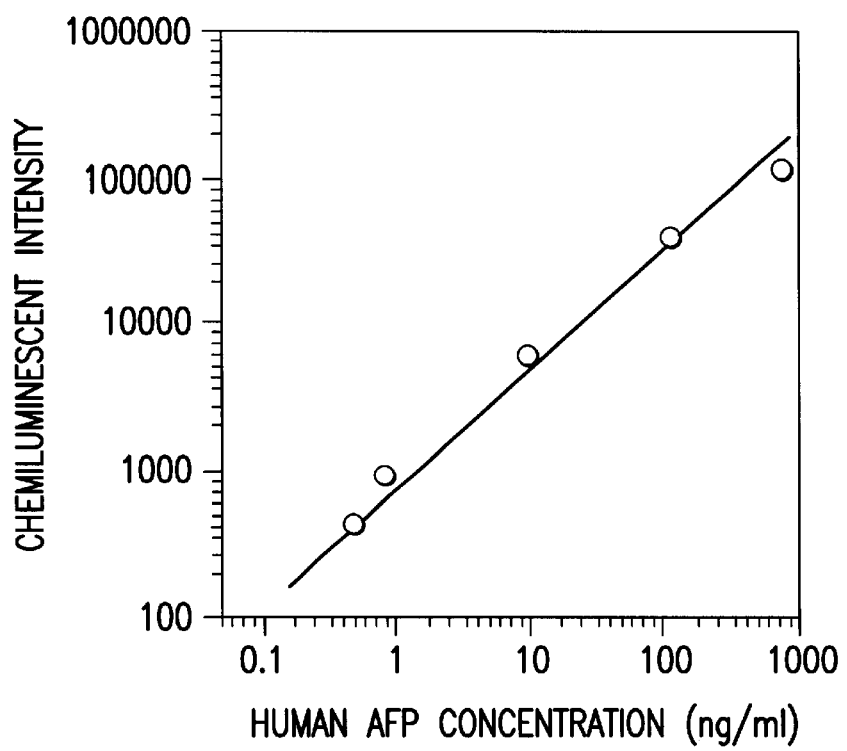
FIG. 6 is a calibration curve for measuring human αAFT as the standard, plotting chemiluminescence intensity of the reaction system of COMPARATIVE EXAMPLE 1-2 against concentration of human αAFT.

50 μL of a PBS solution (pH: 7.4) containing 2% BSA which contained 0 to 800 ng/mL of purified human AFP (standard material) and 100 μL of a PBS solution (pH: 7.4) containing 2% BSA which contained approximately 3 μg/mL of mouse antihuman AFP monoclonal antibody marked with the peroxidase enzyme prepared by REFERENCE EXAMPLE 2 were charged to wells supported by a micro plate, white in color, immobilizing the rabbit antihuman AFP polyclonal antibody prepared by REFERENCE EXAMPLE 1, and the mixture was incubated at 37° C. for 1 hour. The solution was removed from each well under a vacuum, and the well inside was washed with normal saline solution. Then, each well was charged with 250 μL of a 0.1 mM trishydrochloric acid buffer solution (pH: 8.4) containing $4.0 \times 10^{-5}$ M of the chemiluminescent reagent prepared by COMPARATIVE EXAMPLE 1 and $10^{-3}$ M of p-iodophenol, to which 50 μL of a 0.1 M trishydrochloric acid buffer solution (pH: 8.4) containing a 0.0034% aqueous solution of hydrogen peroxide was added, to produce the chemiluminescence. Extent of the chemiluminescence was added up for 0 to 5 sec by a luminometer, to determine luminescent intensity. It was plotted against concentration of the standard material, to prepare the calibration curve (FIG. 6). As shown, the intensity is well correlated with the concentration. This calibration curve can be used to determine concentration of human AFP present in the human serum sample to 0.5 ng/mL.

Comparative Example 1-3
Measurement of β Chain of Human Chorionic Gonadotrophin (βhCG) by the Simultaneous Sandwich CLEIA Method Using the Chemiluminescent Reagent Prepared by Comparative Example 3

Figure 8:
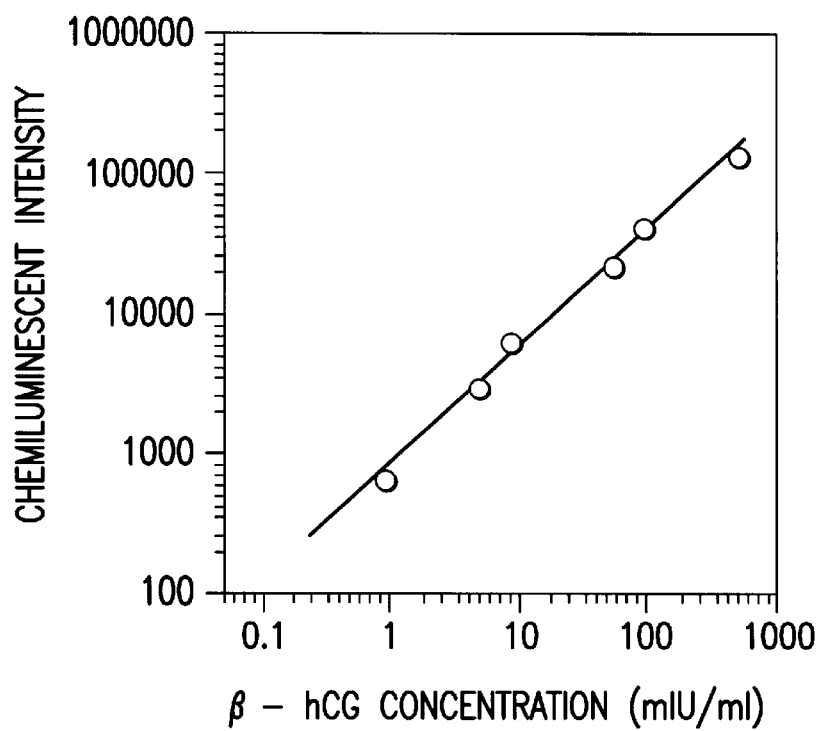
FIG. 8 is a calibration curve for measuring β chain of human chorionic gonadotrophin (βhCG) as the standard, plotting chemiluminescence intensity of the reaction system of COMPARATIVE EXAMPLE 1-3 against concentration of βhCG.

50 μL of a PBS solution (pH: 7.4) containing 2% BSA which contained 0 to 200 mIU/mL of purified βhCG (standard material) and 100 μL of a PBS solution (pH: 7.4) containing 2% BSA which contained approximately 2 μg/mL of mouse anti-βhCG monoclonal antibody marked with the peroxidase enzyme prepared by REFERENCE EXAMPLE 2 were charged to wells supported by a micro plate, white in color, immobilizing the rabbit antihuman βhCG polyclonal antibody prepared by REFERENCE EXAMPLE 1, and the mixture was incubated at 37° C. for 1 hour. The solution was removed from each well under a vacuum, and the well inside was washed with normal saline solution. Then, each well was charged with 250 μL of a 0.1 mM trishydrochloric acid buffer solution (pH: 8.4) containing $4 \times 10^{-5}$ M of the chemiluminescent reagent prepared by COMPARATIVE EXAMPLE 1 and $10^{-3}$ M of p-iodophenol, to which 50 μL of a 0.1 M trishydrochloric acid buffer solution (pH: 8.4) containing a 0.0034% aqueous solution of hydrogen peroxide was added, to produce the chemiluminescence. Extent of the chemiluminescence was added up for 0 to 5 sec by a luminometer, to determine luminescent intensity. It was plotted against concentration of the standard material, to prepare the calibration curve (FIG. 8). This calibration curve can be used to determine concentration of βhCG present in the human serum sample to 1.0 mIU/mL.

Comparative Example 2

Preparation of Chemiluminescent Reagent 1.5 mg of lucigenin was dissolved in 2 mL of N,N-dimethylformamide in a test tube, and the solution was allowed to stand at room temperature for 90 min and incorporated with 2 mL of pure water, to prepare the chemiluminescent reagent.

(Evaluation of chemiluminescent reagent performance)

The same procedure as used for COMPARATIVE EXAMPLE 1 was repeated under the same conditions, to measure chemiluminescence and thereby to evaluate performance of the chemiluminescent reagent. The results are given in Table 1.

Comparative Example 2-1

Measurement of Peroxidase Activity

100 μL of a 0.1 M trishydrochloric acid buffer solution (pH: 8.4) containing $4.0 \times 10^{-5}$ M of the chemiluminescent reagent prepared by COMPARATIVE EXAMPLE 2 and $10^{-3}$ M of p-iodophenol was mixed with 100 μL of a horseradish peroxidase (HRP) solution of varying concentration, to which 50 μL of a 0.0034% aqueous solution of hydrogen peroxide was added, to produce the chemiluminescence. Extent of the chemiluminescence was added up for 0 to 5 sec by a lumino-meter, to determine luminescent intensity. The results are given in Table b. As shown, HRP concentration can be measured up to $1 \times 10^{-18}$ mol/assay.

TABLE b

| HRP (mol/assay) | Luminescence |
| --- | --- |
| 0 | 409 |
| $1 \times 10^{-19}$ | 689 |
| $1 \times 10^{-18}$ | 2500 |
| $1 \times 10^{-17}$ | 18356 |

TABLE b-continued

| HRP (mol/assay) | Luminescence |
| --- | --- |
| $1 \times 10^{-16}$ | 194052 |
| $1 \times 10^{-15}$ | 1390722 |

Comparative Example 2-2

Measurement of Prolactin (PRL) by the Simultaneous Sandwich CLEIA Method Using the Chemiluminescent Reagent Prepared by COMPARATIVE EXAMPLE 2

Figure 7:
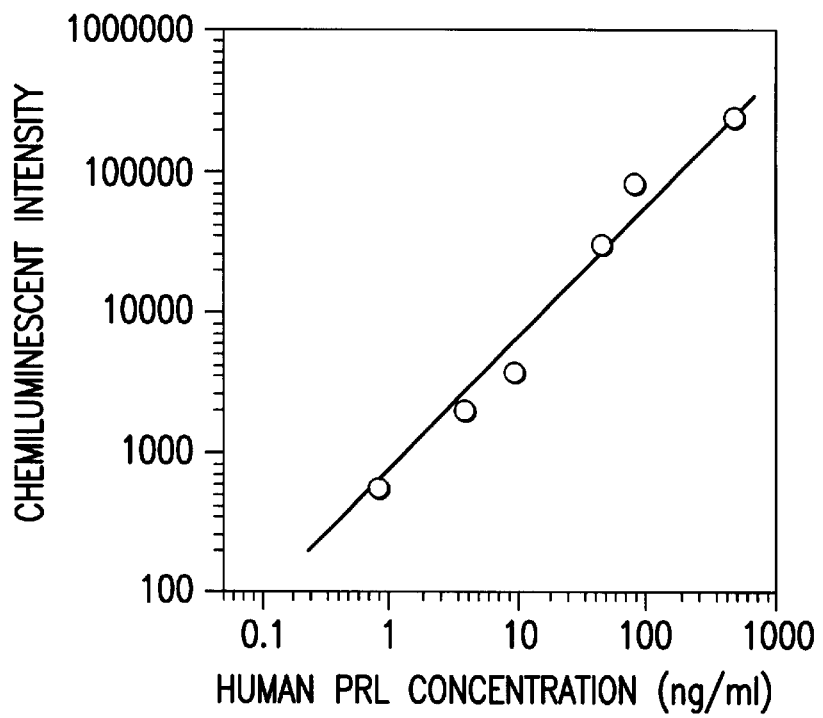
FIG. 7 is a calibration curve for measuring human prolactin (PRL) as the standard, plotting chemiluminescence intensity of the reaction system of COMPARATIVE EXAMPLE 2-2 against concentration of human PRL.

50 μL of a PBS solution (pH: 7.4) containing 2% BSA which contained 0 to 200 ng/mL of purified human PRL (standard material) and 100 μL of a PBS solution (pH: 7.4) containing 2% BSA which contained approximately 2 μg/mL of mouse antihuman PRL monoclonal antibody marked with the peroxidase enzyme prepared by REFERENCE EXAMPLE 2 were charged to wells supported by a micro plate, white in color, immobilizing the rabbit antihuman PRL polyclonal antibody prepared by REFERENCE EXAMPLE 1, and the mixture was incubated at 37° C. for 1 hour. The solution was removed from each well under a vacuum, and the well inside was washed with normal saline solution. Then, each well was charged with 250 μL of a 0.1 mM trishydrochloric acid buffer solution (pH: 8.4) containing $4.0 \times 10^{-5}$ M of the lucigenin-N,N-dimethylacetoamide complex and $10^{-3}$ M of p-iodophenol, to which 50 μL of a 0.1 M trishydrochloric acid buffer solution (pH: 8.4) containing a 0.0034% aqueous solution of hydrogen peroxide was added, to produce the chemiluminescence. Extent of the chemiluminescence was added up for 0 to 5 sec by a luminometer, to determine luminescent intensity. It was plotted against concentration of the standard material, to prepare the calibration curve (FIG. 7). As shown, the intensity is well correlated with the concentration. This calibration curve can be used to determine concentration of human PRL present in the human serum sample to 1.0 ng/mL.

Comparative Example 3

Preparation of Chemiluminescent Reagent 1.5 mg of lucigenin was dissolved in 2 mL of N-methyl-2-pyrrolidone in a test tube, and the solution was allowed to stand at room temperature for 90 min and incorporated with 2 mL of pure water, to prepare the chemiluminescent reagent.

(Evaluation of chemiluminescent reagent performance)

The same procedure as used for COMPARATIVE EXAMPLE 1 was repeated under the same conditions, to measure chemiluminescence. The results are given in Table 1.

Comparative Example 3-1

Measurement of Peroxidase Activity

100 μL of a 0.1 M trishydrochloric acid buffer solution (pH: 8.4) containing $4.0 \times 10^{-5}$ M of the chemiluminescent reagent prepared by COMPARATIVE EXAMPLE 3 and $10^{-3}$ M of p-iodophenol was mixed with 100 μL of a horseradish peroxidase (HRP) solution of varying concentration, to which 50 μL of a 0.0034% aqueous solution of hydrogen peroxide was added, to produce the chemiluminescence. Extent of the chemiluminescence was added up for 0 to 5 sec by a luminometer, to determine luminescent intensity. The results are given in Table c. As shown, HRP concentration can be measured up to $1 \times 10^{-18}$ mol/assay.

TABLE c

| HRP (mol/assay) | Luminescence |
| --- | --- |
| 0 | 486 |
| $1 \times 10^{-19}$ | 646 |
| $1 \times 10^{-18}$ | 1311 |
| $1 \times 10^{-17}$ | 12604 |
| $1 \times 10^{-16}$ | 211206 |

Comparative Example 4
Measurement of Peroxidase Activity Using Luminol

Each of a plurality of wells for chemiluminescence measurement was charged with 200 μL of a 0.1 M trishydrochloric acid buffer solution (pH: 8.4) containing a varying concentration of horseradish peroxidase (HRP) and 20 μL of a trishydrochloric acid buffer solution (pH: 8.4) containing 10 mM of p-iodophenol, to which 50 μL of a 0.1 M trishydrochloric acid buffer solution (pH: 8.4) containing $5.6 \times 10^{-5}$ M of luminol and 50 μL of 0.0034% aqueous solution of hydrogen peroxide were added in this order, to produce the chemiluminescence, extent of which was added up for 0 to 5 sec by a luminometer, to determine luminescent intensity. The results are given in Table d. As shown, HRP concentration can be measured up to $1 \times 10^{-17}$ mol/assay.

TABLE d

| HRP (mol/assay) | Luminescence |
| --- | --- |
| 0 | 36 |
| $1 \times 10^{-18}$ | 60 |
| $1 \times 10^{-17}$ | 81 |
| $1 \times 10^{-16}$ | 297 |
| $1 \times 10^{-15}$ | 20469 |
| $1 \times 10^{-14}$ | 1350786 |

Figure 5:
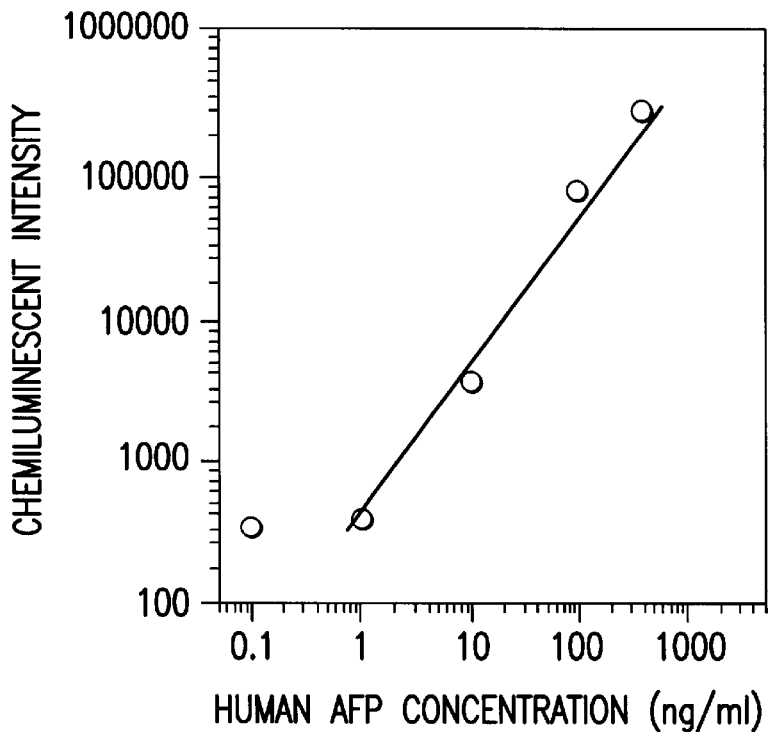
FIG. 5 is a calibration curve for measuring human αAFT as the standard, plotting chemiluminescence intensity of the reaction system of COMPARATIVE EXAMPLE 4-1 against concentration of human αAFT.

Comparative Example 4-1
Measurement of α-fetoprotein (AFP) by the Simultaneous Sandwich CLEIA Method Using the Luminol 50 μL of a PBS solution (pH: 7.4) containing 2% BSA which contained 0 to 800 ng/mL of purified human AFP (standard material) and 100 μL of a PBS solution (pH: 7.4) containing 2% BSA which contained approximately 3 μg/mL of mouse antihuman AFP monoclonal antibody marked with the peroxidase enzyme prepared by REFERENCE EXAMPLE 2 were charged to wells supported by a micro plate, white in color, immobilizing the rabbit antihuman AFP polyclonal antibody prepared by REFERENCE EXAMPLE 1, and the mixture was incubated at 37° C. for 1 hour. The solution was removed from each well under a vacuum, and the well inside was washed with normal saline solution. Then, each well was charged with 100 μL of a 0.1M trishydrochloric acid buffer solution (pH:8.4) containing $10^{-3}$ M of p-iodophenol, to which 100 μL of a 0.1 M trishydrochloric acid buffer solution (pH: 8.4) containing $5.6 \times 10^{-5}$ M of luminol and 50 μL of 0.0034% aqueous solution of hydrogen peroxide were injected, to produce the chemiluminescence, extent of which was added up for 0 to 5 sec by a luminometer, to determine luminescent intensity. It was plotted against concentration of the standard material, to prepare the calibration curve (FIG. 5). As shown, the intensity is correlated with the concentration. This calibration curve can be used to determine concentration of human AFP present in the human serum sample to 2.0 ng/mL.

Reference Example 1
Preparation of Polyclonal Antibody Immobilized on Insoluble Carrier A polyclonal antibody showing a peculiar reaction with an antigen, derived from an animal (e.g., rabbit), was dissolved in a 10 mM phosphate-buffered normal saline solution (PBS, pH: 7.4) to a concentration of 10 μg/mL. 0.1 mL of this solution was charged in each well supported by a micro plate (Lab System Corp.), white in color. It was allowed to stand at 37° C. for 1 hour and washed with PBS, to which 0.3 mL of a 1% aqueous bovine serum albumin (BSA) solution was added. It was then allowed to stand at 37° C. for 1 hour again and treated by post-coating, to prepare the white micro plate immobilizing the polyclonal antibody.

Reference Example 2
Preparation of Monoclonal Antibody Marked with Peroxidase

A monoclonal antibody showing a peculiar reaction with an antigen, derived from a mouse, was dissolved in a 10 mM phosphate-buffered normal saline solution (PBS, pH: 7.4) to a concentration of 1.0 mg/mL. 1 mL of this solution was reacted with 0.1 mL of a dimethylformamide solution containing 10 mg/mL of N-(m-male-imidebenzoic acid)-N-succinimide ester (MBS) at 25° C. for 30 min. The reaction mixture was passed through a column filled with sephadex G-25 for gel filtration with a 0.1 M phosphate buffer solution (pH: 6.0), to separate the MBS-monoclonal reaction product from the unreacted MBS.

A PBS solution containing 1.0 mg/mL of horseradish peroxidase (HRP) as peroxidase enzyme was reacted with an ethanol solution containing 10 mg/mL of N-succinimidyl-3-(2-pyridylthio) propionate (SPDP) at 25° C. for 30 min.

The reaction mixture was passed through a column filled with sephadex G-25 for purification by gel filtration with a 0.1 M phosphate buffer solution (pH: 4.5). The fraction containing the SPDP-HRP reaction product was collected, and enriched approximately 10 times, while it was cooled with ice in a collodion bag. It was then mixed with 1 mL of a 0.1 M acetate-buffered normal saline solution (pH: 4.5) containing a 0.1 M dithiothreitol solution at 25° C. for 30 min, to reduce the pyridyl disulfide group introduced into the HRP molecule. The reaction mixture was passed through a column filled with sephadex G-25 for gel filtration, to obtain the fraction containing the thiol-HRP reaction product.

The mixture of the MBS-monoclonal reaction product and thiol-HRP reaction product was enriched to 4 mg/mL as protein, while it was cooled with ice in a collodion bag. It was then allowed to stand at 4° C. for 24 hours, and passed through a column filled with ultragel AcA44 (SEPRACOR), to obtain the monoclonal antibody marked with peroxidase enzyme.

TABLE 1

| | Luminescence | | | | | | | | | | |
|---|---|---|---|---|---|---|---|---|---|---|---|
| | Examples | | | | | | | | Com. Examples | | |
| HRP (mol/l) | 1 | 2 | 3 | 4 | 5 | 6 | 7 | 8 | 1 | 2 | 3 |
| 0 | 168 | 195 | 381 | 137 | 279 | 614 | 897 | 350 | 544 | 409 | 515 |
| $1 \times 10^{-13}$ | 523 | 462 | 968 | 689 | 1156 | 2668 | 2589 | 1186 | 690 | 1904 | 1663 |
| $1 \times 10^{-12}$ | 2364 | 2508 | 10472 | 9459 | 12177 | 19460 | 18662 | 12942 | 1946 | 10054 | 12850 |
| $1 \times 10^{-11}$ | 25071 | 28114 | 125789 | 129987 | 132176 | 257425 | 205188 | 129418 | 21803 | 127301 | 220408 |
| $1 \times 10^{-10}$ | 605734 | 309663 | 1158954 | 1098131 | 1324564 | 2525468 | 1729505 | 1233783 | 121243 | 1551013 | 742044 |
| $1 \times 10^{-9}$ | 9188068 | 4905576 | 9898434 | 11786664 | 13981533 | — | — | 13476191 | 1710931 | — | — |

Note: HRP: horseradish peroxidase

As described, the chemiluminescent reagent of the present invention, prepared by anyone of EXAMPLES 1 to 8, reacts sensitively with peroxidase at a specific pH level to produce luminescence, extent of which depends on peroxidase concentration, allowing to measure peroxidase of very low concentration. On the other hand, the ones prepared by COMPARATIVE EXAMPLES 1 to 4 produce luminescence of lower intensity and are higher in measurable upper limit concentrations. Comparing the results of EXAMPLES 1-1 to 8-1 with those of COMPARATIVE EXAMPLES 1-1 to 4, it is demonstrated that the chemiluminescent reagent of the present invention has a higher peroxidase activity than the conventional one, and can detect peroxidase of lower concentration.

Comparing the results of EXAMPLES 1-2 to 5-2 with those of COMPARATIVE EXAMPLES 1-2 to 4-1, it is also demonstrated that the chemiluminescent reagent of the present invention can detect trace components, e.g., AFP, PRL and βhCG, at a higher sensitivity.

INDUSTRIAL UTILIZATION OF THE INVENTION

The present invention provides a novel chemiluminescent reagent containing a charge-transferring complex of N,N'-disubstituted-9,9'-bisacridinium salt, and high-sensitivity chemiluminescent analysis method using the same, in particular useful for measuring peroxidase activity and enzyme immunoassay, which can greatly contribute to commercialization of the high-sensitivity chemiluminescent analysis technology for various areas, e.g., clinic, food and animal/plant tests.

What is claimed is:

1. A chemiluminescent reagent composition characterized by the chemiluminescence produced in the presence of a peroxide, intensity of which varies depending on concentration of peroxidase enzyme, and comprising, as the major ingredients, a charge-transferring complex of N,N'-disubstituted-9,9'-bisacridinium salt, expressed by a broad absorption band having a maximum at around 550 nm in the ultraviolet absorption spectrum and shown by the general formula (1):

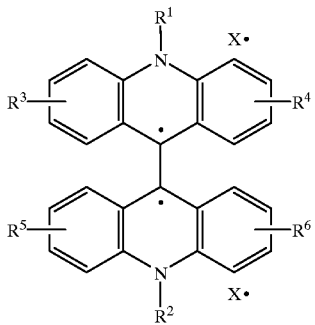

(1)

(wherein, $R^1$ and $R^2$ are each selected from the group consisting of an alkyl, aryl and halogenated aryl groups, and may be the same or different; $R^3$, $R^4$, $R^5$ and $R^6$ are each selected from the group consisting of hydrogen, alkyl, aryl, alkoxy and aryloxy groups and halogen, and may be the same or different; and X· is an acid radical as the residue left by the electron transferring from the counter anion of the bisacridinium salt as the precursor), and an N,N-disubstituted carboxylic amide compound shown by the general formula (2):

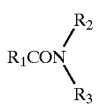

(2)

(wherein, $R_1$ is selected from the group consisting of hydrogen, alkyl group having a carbon number of 1 to 10, an alkenyl group having a carbon number of 2 to 10 and an aryl group having a carbon number of 6 to 20, wherein the aryl group may be substituted with an alkyl, nitro, hydroxyl or amino group, halogen or the like; $R_2$ is selected from the group consisting of methyl and ethyl groups; and $R_3$ is selected from the group consisting of an alkyl group having a carbon number of 1 to 10, an alkenyl group having a carbon number of 2 to 10 and an aryl group having a carbon number of 6 to 20, wherein the aryl group may be substituted with an alkyl, nitro, hydroxyl or amino groups, halogen, and $R_1$ and $R_3$ may be bonded to each other to form a ring together with the carbon atom and nitrogen atom which are in the amide group, respectively, to which each of $R_1$ and $R_3$ are bonded).

2. A chemiluminescent reagent characterized by the chemiluminescent produced in the presence of a peroxide, extent of which varies depending on concentration of peroxidase enzyme, and comprising, as the major ingredients, a charge-transferring complex of N,N'-disubstituted-9,9'-bisacridium salt, shown by the general formula (1), N,N-disubstituted carboxylic amide compound shown by the general formula (2), respectively expressed in claim 1, and aminoalcohol compound shown by the general formula (3)

$(HOR)_m NH_{3-m}$ (3)

(wherein R is a divalent aliphatic hydrocarbon group having a carbon number of 1 to 5; and (m) is an integer of 1 to 3).

3. The chemiluminescent reagent of claim 1 or 2, wherein said $R^1$ and $R^2$ are each selected from the group consisting of an alkyl, aryl and halogenated aryl groups having a carbon number of 1 to 20; and $R^3$, $R^4$, $R^5$ and $R^6$ are each selected from the group consisting of hydrogen and halogen atoms, and an alkyl, aryl, alkoxy and aryloxy groups having a carbon number of 1 to 20 for the general formula (1).

4. The chemiluminescent reagent of claim 1, wherein said $R^1$ and $R^2$ are each selected from the group consisting of an alkyl group having a carbon number of 1 to 10, and aryl and halogenated aryl groups having a carbon number of 6 to 20; and $R^3$, $R^4$, $R^5$ and $R^6$ are each selected from the group consisting of hydrogen and halogen atoms, and an alkyl group having a carbon number of 1 to 10, and aryl, alkoxy and aryloxy groups having a carbon number of 6 to 20.

5. The chemiluminescent reagent of claim 4, wherein said $R^1$ and $R^2$ are each selected from the group consisting of an alkyl group having a carbon number of 1 to 10, and aryl and halogenated aryl groups having a carbon number of 6 to 20; and $R^3$, $R^4$, $R^5$ and $R^6$ are each hydrogen atom.

6. The chemiluminescent reagent of claim 1 or 2, wherein said N,N'-disubstituted-9,9'-bisacridinium salt for the charge-transferring complex is selected from the group consisting of N,N'-dimethyl-9,9'-bisacridinium di-nitrate, N,N'-dimethyl-9,9'-bisacridinium dihydrochloride, and N,N'-dimethyl-9,9'-bisacridinium dihydroiodide.

7. The chemiluminescent reagent of claim 1 or 2, wherein said N,N'-disubstituted carboxylic acid is selected from the group consisting of N,N'-dimethylformamide, N,N'-dimethylacetoamide and N-methyl-2-pyrrolidone.

8. The chemiluminescent reagent of claim 1 or 2, wherein said aminoalcohol compound is selected from the group consisting of monoalkanolamine, dialkanolamine and trialkanolamines.

9. A chemiluminscent reagent prepared by reacting, in the presence of irradiated light, an N,N'-disubstituted-9,9'-bisacridinium salt shown by the general formula (1A):

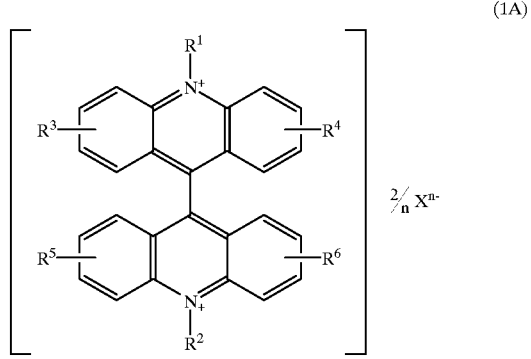

(1A)

(wherein, $R^1$ and $R^2$ are each selected from the group consisting of an alkyl, aryl and halogenated aryl groups, and may be the same or different; $R^3$, $R^4$, $R^5$ and $R^6$ are each selected from the group consisting of hydrogen, alkyl, aryl, alkoxy and aryloxy groups and halogen, and may be the same or different; and $X^{n-}$ is an n-valent anion and (n) is 1 or 2, with an N,N-disubstituted carboxylic amide compound shown by the general formula (2):

(2)

(wherein, $R_1$ is selected from the group consisting of hydrogen, alkyl group having a carbon number of 1 to 10, an alkenyl group having a carbon number of 2 to 10 and an aryl group having a carbon number of 6 to 20, wherein the aryl group may be substituted with an alkyl, nitro, hydroxyl or amino group, and halogen; $R_2$ is selected from the group consisting of methyl and ethyl groups; and $R_3$ is selected from the group consisting of an alkyl group having a carbon number of 1 to 10, an alkenyl group having a carbon number of 2 to 10 and an aryl group having a carbon number of 6 to 20, wherein the aryl group may be substituted with an alkyl, nitro, hydroxyl or amino groups, halogen, and $R_1$ and $R_3$ may be bonded to each other to form a ring together with the carbon atom and nitrogen atom which are in the amide group, respectively, to which each of $R_1$ and $R_3$ are bonded).

10. The chemiluminescent reagent of claim 9, prepared by reacting an N,N'-disubstituted-9,9'-bisacridinium salt shown by the general formula (1A) with N,N'-disubstituted carboxylic amide compound shown by the general formula (2) while being irradiated with light, wherein an aminoalcohol compound shown by the general formula (3) of claim 1 is added to the reaction system during and/or after the reaction.

11. The chemiluminescent reagent of claim 9, wherein said $R^1$ and $R^2$ are each selected from the group consisting of an alkyl, aryl and halogenated aryl groups having a carbon number of 1 to 20; and $R^3$, $R^4$, $R^5$ and $R^6$ are each selected from the group consisting of hydrogen and halogen atoms, and an alkyl, aryl, alkoxy and aryloxy groups having a carbon number of 1 to 20 for the general formula (1A).

12. The chemiluminescent reagent of any one of claims 9 to 11, wherein said $R^1$ and $R^2$ are each selected from the group consisting of an alkyl group having a carbon number of 1 to 10, and aryl and halogenated aryl groups having a carbon number of 6 to 20; and $R^3$, $R^4$, $R^5$ and $R^6$ are each selected from the group consisting of hydrogen and halogen atoms, and an alkyl group having a carbon number of 1 to 10, and an aryl, alkoxy and aryloxy groups having a carbon number of 6 to 20.

13. The chemiluminescent reagent of claim 12, wherein said $R^1$ and $R^2$ are each selected from the group consisting of an alkyl group having a carbon number of 1 to 10, and an aryl and halogenated aryl groups having a carbon number of 6 to 20; and $R^3$, $R^4$, $R^5$ and $R^6$ are each hydrogen atom.

14. The chemiluminescent reagent of any one of claim 9 or 10, wherein said N,N'-disubstituted-9,9'-bisacridinium salt is selected from the group consisting of N,N'-dimethyl-9,9'-bisacridinium dinitrate, N,N'-dimethyl-9,9'-bisacridinium dihydrochloride, and N,N'-dimethyl-9,9'-bisacridinium dihydroiodide.

15. The chemiluminescent reagent of claim 9 or 10, wherein the light source for said light irradiation emits visible light.

16. A chemiluminescent analysis method for measuring peroxidase activity in the presence of a hydrogen acceptor, which comprises measuring peroxidase activity with a chemiluminescent reagent composition of any one of claims 1, 2, 9 and 10.

17. The chemiluminescent analysis method for measuring peroxidase activity of claim 16, wherein further used is a luminescent promoter composed of at least one type of phenolic compound selected from the group consisting of p-iodophenol, p-phenylphenol and 6-hydroxybenzothiazole, for measuring peroxidase enzyme activity in the presence of the hydrogen acceptor.

18. A chemiluminescent enzyme immunoassay, which comprises mixing an antibody or antigen marked with peroxidase enzyme with an antigen, antibody or agglomerate thereof in a sample to be analyzed to form the immune complex from the marker/antigen-antibody complex by the antigen-antibody reaction, separating the immune complex, producing its chemiluminescence in the presence of a hydrogen acceptor by the aid of the the chemiluminescent reagents of one of claims 1, 2, 9 and 10, and measuring the luminescence intensity to quantitatively analyze the antigen or antibody in the sample.

19. The chemiluminescent enzyme immunoassay of claim 18, wherein said antigen-antibody reaction is effected in the presence of the antigen immobilized on an insoluble carrier, and the immune complex marked with the peroxidase enzyme is formed on said carrier.

20. A method of chemiluminescent analysis using a chemiluminescent reagent composition characterized by measuring the chemiluminescence produced in the presence of a peroxide, intensity of which varies depending on concentration of peroxidase enzyme, and comprising, as the major ingredients, a charge-transferring complex of N,N'-disubstituted-9,9'-bisacridinium salt, shown by the general formula (1):

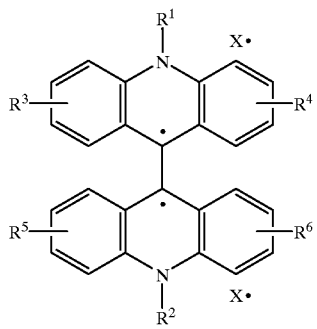

(1)

(wherein, $R^1$ and $R^2$ are each selected from the group consisting of an alkyl, aryl and halogenated aryl groups, and may be the same or different; $R^3$, $R^4$, $R^5$ and $R^6$ are each selected from the group consisting of hydrogen, alkyl, aryl, alkoxy and aryloxy groups and halogen, and may be the same or different; and X· is an acid radical as the residue left by the electron transferring from the counter anion of the bisacridinium salt as the precursor), and an N,N-disubstituted carboxylic amide compound shown by the general formula (2):

(2)

(wherein, $R_1$ is selected from the group consisting of hydrogen, alkyl group having a carbon number of 1 to 10, an alkenyl group having a carbon number of 2 to 10 and an aryl group having a carbon number of 6 to 20, wherein the aryl group may be substituted with an alkyl, nitro, hydroxyl or amino group, and halogen; $R_2$ is selected from the group consisting of methyl and ethyl groups; and $R_3$ is selected from the group consisting of an alkyl group having a carbon number of 1 to 10, an alkenyl group having a carbon number of 2 to 10 and an aryl group having a carbon number of 6 to 20, wherein the aryl group may be substituted with an alkyl, nitro, hydroxyl or amino groups, halogen, and $R_1$ and $R_3$ may be bonded to each other to form a ring together with the carbon atom and nitrogen atom which are in the amide group, respectively, to which each of $R_1$ and $R_3$ are bonded).

* * * * *